(12) United States Patent
Moravec et al.

(10) Patent No.: US 12,222,271 B2
(45) Date of Patent: Feb. 11, 2025

(54) DROPLET SENSORS FOR FUEL SYSTEMS

(71) Applicant: Donaldson Company, Inc., Minneapolis, MN (US)

(72) Inventors: Davis B. Moravec, Burnsville, MN (US); Daryl L. Quam, Bloomington, MN (US); Cullen E. Hall, Chaska, MN (US); Brian R. Tucker, Farmington, MN (US); Andrew J. Dallas, Lakeville, MN (US)

(73) Assignee: Donaldson Company, Inc., Bloomington, MN (US)

( * ) Notice: Subject to any disclaimer, the term of this patent is extended or adjusted under 35 U.S.C. 154(b) by 320 days.

(21) Appl. No.: 17/059,189

(22) PCT Filed: May 31, 2019

(86) PCT No.: PCT/US2019/034809
§ 371 (c)(1),
(2) Date: Nov. 25, 2020

(87) PCT Pub. No.: WO2019/232305
PCT Pub. Date: Dec. 5, 2019

(65) Prior Publication Data
US 2021/0223154 A1 Jul. 22, 2021

Related U.S. Application Data

(60) Provisional application No. 62/678,806, filed on May 31, 2018.

(51) Int. Cl.
*G01N 15/0205* (2024.01)
*F02M 37/26* (2019.01)
*F02M 37/32* (2019.01)
*G01F 1/74* (2006.01)
*G01F 23/292* (2006.01)
*G01N 15/06* (2024.01)
*G01N 33/28* (2006.01)
*G01N 15/075* (2024.01)

(52) U.S. Cl.
CPC ......... *G01N 15/0205* (2013.01); *F02M 37/26* (2019.01); *F02M 37/32* (2019.01);
(Continued)

(58) Field of Classification Search
CPC .... G01N 15/0205; G01N 15/06; G01N 33/28; G01N 2015/0693; F02M 37/26; F02M 37/32; G01F 1/74; G01F 23/292
See application file for complete search history.

(56) References Cited

U.S. PATENT DOCUMENTS

| 4,219,411 A | 8/1980 | Molday et al. |
| 4,656,869 A * | 4/1987 | Zacharias ............ G01N 29/024 73/61.44 |

(Continued)

FOREIGN PATENT DOCUMENTS

| CN | 101765762 A | 6/2010 |
| CN | 105008895 A | 10/2015 |

(Continued)

OTHER PUBLICATIONS

Amini, et al., "Inertial microfluidic physics", Jan. 1, 2014, Lab on a Chip, 14(15):2739-2761.
(Continued)

*Primary Examiner* — Edmond C Lau
*Assistant Examiner* — Jarreas Underwood
(74) *Attorney, Agent, or Firm* — Mueting Raasch Group

(57) ABSTRACT

A droplet detection system includes a sensing channel, such as a microfluidic channel, configured to receive a flow of fluid that may contain one or more liquid droplets dispersed in the fluid. The cross-sectional area of the sensing channel maybe configured to allow droplets of a predetermined size to flow through the channel one at a time. A light source, a light aperture, and a light detector are positioned outside the sensing channel, which use light in a selected frequency
(Continued)

band that has a substantially different absorbance for the liquid compared to the fluid. Liquid droplets may be detected and characterized using a signal from the light detector.

13 Claims, 18 Drawing Sheets

(52) U.S. Cl.
CPC .............. *G01F 1/74* (2013.01); *G01F 23/292* (2013.01); *G01N 15/06* (2013.01); *G01N 33/28* (2013.01); *G01N 15/075* (2024.01)

(56) References Cited

U.S. PATENT DOCUMENTS

| | | | |
|---|---|---|---|
| 5,213,682 A | 5/1993 | Richardson | |
| 5,349,188 A | 9/1994 | Maggard | |
| 5,534,708 A | 7/1996 | Ellinger et al. | |
| 5,681,749 A | 10/1997 | Ramamoorthy | |
| 5,690,895 A * | 11/1997 | Matsumoto | G01N 21/05 356/73 |
| 5,717,209 A | 2/1998 | Bigman et al. | |
| 5,958,237 A | 9/1999 | Cort et al. | |
| 6,134,951 A * | 10/2000 | Scott | G01F 1/74 73/861.04 |
| 6,136,171 A * | 10/2000 | Frazier | B81C 1/00357 209/127.1 |
| 6,865,926 B2 | 3/2005 | Obrien et al. | |
| 7,214,298 B2 | 5/2007 | Spence et al. | |
| 7,575,681 B2 | 8/2009 | Angelescu et al. | |
| 7,679,059 B2 | 3/2010 | Zhou | |
| 7,932,490 B2 * | 4/2011 | Wang | G01N 15/0205 73/30.01 |
| 7,966,892 B1 * | 6/2011 | Halilah | G01F 15/08 73/861.04 |
| 8,186,913 B2 | 5/2012 | Toner et al. | |
| 8,208,138 B2 | 6/2012 | Papautsky et al. | |
| 8,226,332 B2 | 7/2012 | Kojima et al. | |
| 8,276,760 B2 | 10/2012 | Lean et al. | |
| 8,405,033 B2 | 3/2013 | Debreczeny | |
| 8,426,209 B2 | 4/2013 | Butler et al. | |
| 8,461,519 B2 * | 6/2013 | Lievois | G01N 21/314 250/269.1 |
| 8,693,762 B2 | 4/2014 | Di Carlo et al. | |
| 8,784,012 B2 | 7/2014 | Toner et al. | |
| 8,807,879 B2 | 8/2014 | Toner et al. | |
| 8,931,644 B2 | 1/2015 | Lean et al. | |
| 9,090,865 B2 | 7/2015 | Di Carlo et al. | |
| 9,133,499 B2 | 9/2015 | Di Carlo et al. | |
| 9,347,595 B2 | 5/2016 | Toner et al. | |
| 9,433,880 B2 | 9/2016 | Lean et al. | |
| 9,458,489 B2 | 10/2016 | Lim et al. | |
| 9,551,651 B2 | 1/2017 | Hegeman et al. | |
| 9,644,229 B2 | 5/2017 | Brubacher | |
| 9,645,149 B2 | 5/2017 | Nagrath et al. | |
| 9,651,501 B2 | 5/2017 | Müller et al. | |
| 9,789,485 B2 | 10/2017 | Han et al. | |
| 9,797,791 B2 | 10/2017 | Vogt et al. | |
| 9,804,068 B2 | 10/2017 | Burke et al. | |
| 9,808,803 B2 | 11/2017 | Toner et al. | |
| 9,841,331 B2 | 12/2017 | Wood et al. | |
| 9,949,679 B2 | 4/2018 | Renlund | |
| 9,968,869 B2 | 5/2018 | Volkel et al. | |
| 9,987,632 B2 | 6/2018 | Papautsky et al. | |
| 10,001,496 B2 * | 6/2018 | Jung | G01N 35/00871 |
| 10,047,344 B2 | 8/2018 | Poon et al. | |
| 10,052,571 B2 | 8/2018 | Lean et al. | |
| 10,073,024 B2 | 9/2018 | Nagrath et al. | |
| 10,077,462 B2 | 9/2018 | Hou et al. | |
| 10,130,946 B2 | 11/2018 | Nagrath et al. | |
| 10,144,009 B2 | 12/2018 | Bhagat et al. | |
| 10,238,995 B2 | 3/2019 | Volkel et al. | |
| 2002/0014224 A1 * | 2/2002 | Ismailov | F02D 41/40 123/494 |
| 2003/0085180 A1 * | 5/2003 | Akins | G06Q 40/08 210/138 |
| 2008/0128331 A1 | 6/2008 | Lean et al. | |
| 2008/0213821 A1 | 9/2008 | Liu et al. | |
| 2008/0237503 A1 * | 10/2008 | Albertson | G01N 33/2847 250/564 |
| 2009/0050538 A1 | 2/2009 | Lean et al. | |
| 2009/0101822 A1 | 4/2009 | Mitra et al. | |
| 2009/0114607 A1 | 5/2009 | Lean et al. | |
| 2009/0145392 A1 | 6/2009 | Clark et al. | |
| 2009/0283452 A1 | 11/2009 | Lean et al. | |
| 2011/0000560 A1 * | 1/2011 | Miller | B01F 35/2202 137/561 R |
| 2011/0095190 A1 * | 4/2011 | Kommareddy | G01N 23/207 701/100 |
| 2011/0096327 A1 | 4/2011 | Papautsky et al. | |
| 2011/0259802 A1 | 10/2011 | Wieczorek et al. | |
| 2012/0085147 A1 * | 4/2012 | Werner | G01N 33/2835 250/288 |
| 2012/0112072 A1 | 5/2012 | Jones et al. | |
| 2012/0152814 A1 | 6/2012 | Lean et al. | |
| 2012/0162654 A1 | 6/2012 | Webb et al. | |
| 2013/0042893 A1 * | 2/2013 | Ariessohn | G01N 1/2202 137/560 |
| 2013/0130226 A1 | 5/2013 | Lim et al. | |
| 2013/0210058 A1 | 8/2013 | White et al. | |
| 2013/0301053 A1 * | 11/2013 | Carmignani | G01N 21/39 356/437 |
| 2014/0263824 A1 * | 9/2014 | Pesyna | B64D 33/02 244/58 |
| 2015/0268244 A1 | 9/2015 | Cho et al. | |
| 2015/0276589 A1 * | 10/2015 | Wagner | G01N 15/1404 356/440 |
| 2016/0121331 A1 | 5/2016 | Kapur et al. | |
| 2016/0231223 A1 | 8/2016 | Wang et al. | |
| 2016/0348561 A1 * | 12/2016 | Higashi | F01N 11/007 |
| 2017/0205338 A1 | 7/2017 | Coates | |
| 2017/0292104 A1 | 10/2017 | Ebrahimi Warkiani et al. | |
| 2018/0369817 A1 | 12/2018 | Rezai et al. | |
| 2020/0407671 A1 | 12/2020 | Baltekin et al. | |
| 2021/0121843 A1 | 4/2021 | Matsuoka et al. | |
| 2022/0395768 A1 | 12/2022 | Moravec et al. | |
| 2023/0356116 A1 | 11/2023 | Moravec et al. | |
| 2023/0390769 A1 | 12/2023 | Nelson et al. | |
| 2024/0001263 A1 | 1/2024 | Moravec et al. | |

FOREIGN PATENT DOCUMENTS

| | | | |
|---|---|---|---|
| CN | 105987870 | 10/2016 | |
| CN | 107110766 A | 8/2017 | |
| DE | 3712879 A1 | 11/1988 | |
| EP | 0 494 734 | 7/1992 | |
| EP | 2 123 361 | 11/2009 | |
| WO | 2008/130977 A2 | 10/2008 | |
| WO | 2010/111231 | 9/2010 | |
| WO | WO-2010111231 A1 * | 9/2010 | .......... B01F 13/0071 |
| WO | 2011/027099 | 3/2011 | |
| WO | 2014/062719 | 4/2014 | |
| WO | 2018/201034 A1 | 11/2018 | |
| WO | 2021/108692 | 6/2021 | |
| WO | 2022/115619 | 6/2022 | |
| WO | 2022/256537 | 12/2022 | |
| WO | 2023/235396 A1 | 12/2023 | |

OTHER PUBLICATIONS

Asghari, et al., "Tape'n roll inertial microfluidics", 2019, Sensors and Actuators A: Physical, 299:111630, 9 pages. Available online Sep. 20, 2019.

Asmolov, "The inertial lift on a spherical particle in a plane Poiseuille flow at large channel Reynolds number," 1999, J Fluid Mech, 381:63-87.

Chen, et al., "Capacitive sensing of droplets for microfluidic devices based on thermocapillary actuation," 2004, Lab Chip 4(5):473-480. Published online Jun. 25, 2004.

(56) References Cited

OTHER PUBLICATIONS

Dean, "XVI. Note on the motion of fluid in a curved pipe," The London, Edinburgh, and Dublin Philosophical Magazine and Journal of Science Series 7, 1927, 4(20):208-223, and bibliographic page.

Di Carlo, "Inertial Microfluidics," 2009, Lab Chip, 9(21):3038-3046. Available online Sep. 22, 2009.

Di Carlo, et al., "Continuous inertial focusing, ordering, and separation of particles in microchannels," Nov. 27, 2007, Proc Natl Acad Sci U S A 104(48):18892-18897.

Dombrovsky, et al., "Spectral properties of diesel fuel droplets," Jan. 2003, 82(1):15-22. Available online Jul. 18, 2002.

Dong, et al., "Capacitance Variation Induced by Microfluidic Two-Phase Flow across Insulated Interdigital Electrodes in Lab-On-Chip Devices," Jan. 26, 2015, Sensors 15(2):2694-2708.

Elbuken, et al., "Detection of microdroplet size and speed using capacitive sensors," Sensors and Actuators A: Physical, 2011, 171(2):55-62.

Garstecki, et al., "Formation of droplets and bubbles in a microfluidic T-junction—scaling and mechanism of break-up," 2006, Lab Chip, 6:437-446. Available online Jan. 25, 2006.

Gossett, et al., "Particle Focusing Mechanisms in Curving Confined Flows," Oct. 15, 2009, Analytical Chemistry, 31(20):8459-8465. Available online Sep. 17, 2009.

Guchardi, et al., "Evaluation of a Dual-Beam Near-Infrared Spectrometer Based on Acousto-optic Tunable Filters", Dec. 31, 2001, Applied Spectroscopy, 55(4):454-457.

International Application No. PCT/US2021/060842 filed Nov. 24, 2021, PCT International Search Report and Written Opinion mailed Mar. 16, 2022, 12 pages.

International Patent Application No. PCT/US2019/034809 filed May 31, 2019, PCT International Preliminary Report on Patentability issued Dec. 1, 2020, 11 pages.

International Patent Application No. PCT/US2019/034809 filed May 31, 2019, PCT International Search Report and Written Opinion issued Oct. 28, 2019, 17 pages.

International Patent Application No. PCT/US2019/034809 filed May 31, 2019, PCT Invitation to Pay Additional Fees issued Sep. 5, 2019, 11 pages.

International Patent Application No. PCT/US2020/062401, filed Nov. 25, 2020, International Search Report and Written Opinion, mailed Mar. 22, 2021, 17 pages.

International Patent Application No. PCT/US2020/062401, filed Nov. 25, 2020, Invitation to Pay Additional Fees and Communication Relating to the Results of the Partial International Search, mailed Feb. 1, 2021, 11 pages.

International Patent Application No. PCT/US2020/062401, filed Nov. 25, 2020, PCT International Preliminary Report on Patentability, issued May 17, 2022, 11 pages.

International Patent Application No. PCT/US2022/031972 filed Jun. 2, 2022, PCT International Search Report and Written Opinion issued Oct. 4, 2022, 17 pages.

Johnston, et al., "Dean flow focusing and separation of small microspheres within a narrow size range," 2014, Microfluidics and Nanofluidics, 17(3):509-518. Published online Jan. 23, 2014.

Kim, et al., "Hydrodynamic Effects on Spectroscopic Water Detection in Gasoline Pipe Flow", Jun. 18, 2014, Energies, 7(6):3810-3822. Available online at https://www.mdpi.com/1996-1073/7/6/3810. Retrieved from the internet on Aug. 9, 2021.

Kuntaegowdanahalli, et al., "Inertial microfluidics for continuous particle separation in spiral microchannels," 2009, Lab Chip, 9(20):2973-2980. Available online Jul. 21, 2009.

Lancaster, et al. (PARC, Inc.), "Hydrodynamic Separation of Neutrally Buoyant Particles From Wastewater: Reducing Energy Demands and Increasing Energy Yields," Mar. 2015, California Energy Commission. Publication humber. CEC-500-2016-025, 96 pages.

Liu, et al., "Microfluidic CODES: a scalable multiplexed electronic sensor for orthogonal detection of particles in microfluidic channels," Lab Chip 2016, 16(8):1350-1357.

Murali, "A Microfluidic Coulter Counting Device for Metal Wear Detection in Lubrication Oil," University of Akron, Dec. 2008, 97 pages.

Nivedita, et al., "Dean Flow Dynamics in Low-Aspect Ratio Spiral Microchannels," Mar. 10, 2017, Sci. Rep., 7:44072, 10 pages.

Nivedita, et al., "Use of Secondary Dean Vortices in Spiral Microchannels for Cell Separations," 18th International Conference on Miniaturized Systems for Chemistry and Life Sciences, San Antonio, Texas, USA, Oct. 26-30, 2014, pp. 2483-2485.

Shields IV, et al., "Microfluidic cell sorting: a review of the advances in the separations of cells from debulking to rare cell isolation," 2015, Lab on a Chip, 15:1230-1249. Available online Jan. 6, 2015.

Völkel, et al., "Innovative Technology for Selective Contaminant Removal," 2011, NSTI-Nanotech 2011, 3:581-584.

Wang, et al., "A low-cost, plug-and-play inertial microfluidic helical capillary device for high-throughput flow cytometry," 2017, Biomicrofluidics, 11(1):014107, 11 pages. Available online Jan. 30, 2017.

Warkiani, et al., "Membrane-less microfiltration using inertial microfluidics," Jul. 8, 2015, Scientific Reports, 5:11018., 10 pages.

Wu, "Microfluidic Hydrodynamic Cell Separation: A Review", 2009, Micro and Nanosystems, 1(3):1-12.

Yuan, "In-Line Microfluidic Particle Preconcentrator and Detector for Continuos Flow Monitoring" PhD diss., University of Tennessee—Knoxville, Aug. 2014, 140 pages.

Zheng, et al., "The influence of Saffman lift force on nanoparticle concentration distribution near a wall," 2009, Applied Physics Letters, 95(12):124105, 4 pages. Available online Sep. 25, 2009.

Zhou, et al., "Fundamentals of inertial focusing in microchannels," 2013, Lab Chip 13(6):1121-1132.

Beech, et al., "Tipping the balance of deterministic lateral displacement devices using dielectrophoresis", 2009, Lab on a Chip, 9:2698-2706. Available online Jun. 15, 2009.

Chinese Patent Application No. 201980043432.1, Third Office Action issued Feb. 27, 2023, 14 pages. With English translation.

Di Carlo, et al., "Equilibrium Separation and Filtration of Particles Using Differential Inertial Focusing", Mar. 15, 2008, Analytical Chemistry, 80(6):2204-2211.

Holm, et al., "Separation of parasites from human blood using deterministic lateral displacement", 2011, Lab on a Chip, 11:1326-1332.

Lee, et al., "Inertial focusing of particles with an aerodynamic lens in the atmospheric pressure range", 2003, Journal of Aerosol Science, 34:211-224.

Nugen, et al., "PMMA biosensor for nucleic acids with integrated mixer and electrochemical detection", 2009, Biosensors and Bioelectronics, 24:2428-2433. Available online Dec. 25, 2008.

Optek Process Photometry—Sensor Summary, Product Information Sheet, 2006, optek-Danulat, Inc., Germantown, Wisconsin. 2 pages.

Russom, et al., "Differential inertial focusing of particles in curved low-aspect-ratio microchannels", Jul. 31, 2009, New Journal of Physics, 11:075025, 10 pages. Available online at http://www/njp.org/.

Xu, et al., "Detection of Cryptosporidium parvum in buffer and in complex matrix using PEMC sensors at 5 oocysts mL-1," 2010, Analytica Chimica Acta 669:81-86. Available online May 17, 2010.

Xu, "Photoelectric Detection Technology and System Design", Aug. 2013, National Defense Industry Press, title page, publishing information page, and pp. 240-241. No translation provided. See Chinese Patent Application No. 201980043432.1 Third Office Action issued Feb. 27, 2023 for statement of relevance.

\* cited by examiner

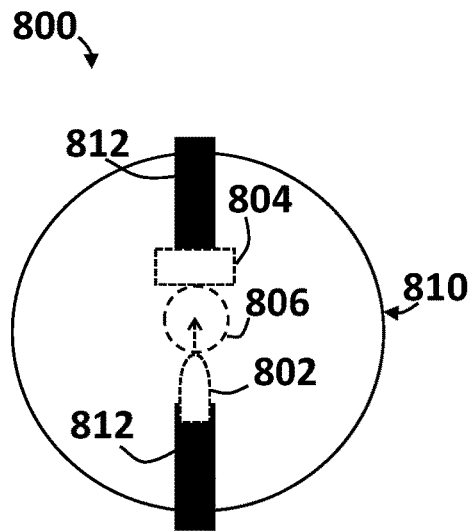
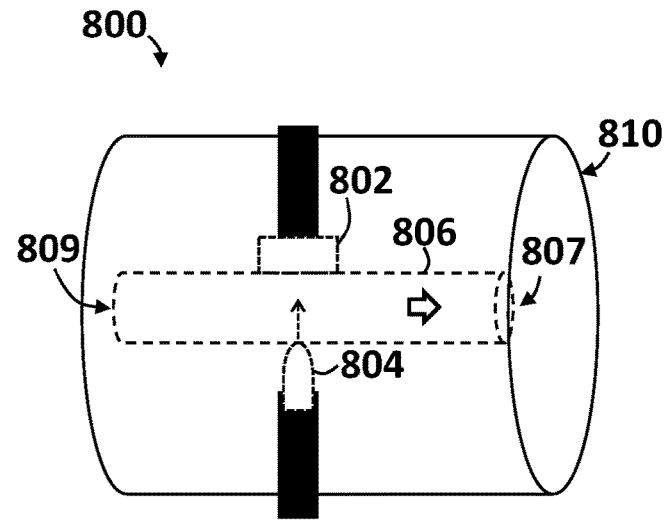
FIG. 14A  FIG. 14B
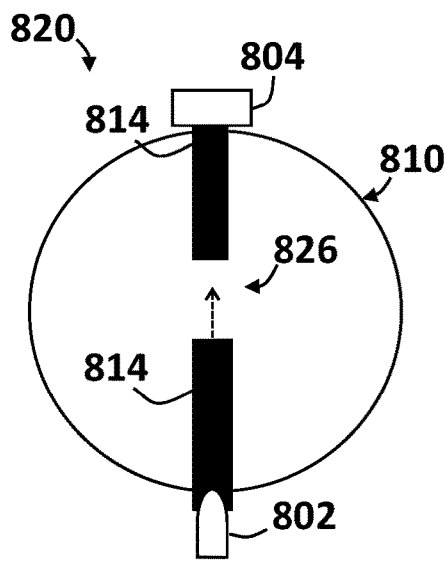
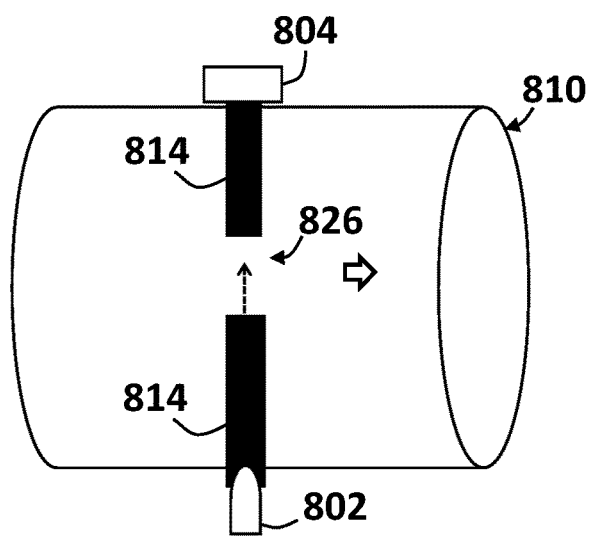
FIG. 15A  FIG. 15B

DROPLET SENSORS FOR FUEL SYSTEMS

The present application is the § 371 U.S. National Stage of International Application No. PCT/US2019/034809, filed 31 May 2019, which claims the benefit of U.S. Provisional Application Ser. No. 62/678,806, filed May 31, 2018, which is incorporated by reference into this disclosure.

The present disclosure relates to droplet sensors. In particular, the present disclosure relates to droplet sensors configured to detect liquid droplets dispersed in a different fluid, such as water droplets dispersed in fuel.

The water in fuel may be problematic in fuel systems of internal combustion engines. Water in fuel may damage fuel injectors due to corrosion or vaporization during combustion. For example, damage to injectors may cause various problems in operation of the engine, such as failing to be able to comply with jurisdictional emission standards. Fuel injector damage may require repair or maintenance. Reduced operating time may be particularly costly for commercial or industrial vehicles.

Sensors, such as water-in-fuel (WIF) sensors, have been proposed to detect water in fuel. One type of sensor is a float system, which uses material with density between water and fuel. Another type of sensor is a conductivity sensor. Both of these types of sensors are subject to problems over time as dirt or debris collects on the surfaces. In particular, conductive WIF sensors may be susceptible to corrosion and electrochemical plating over time. In-line flow sensors on fuel systems have been proposed using light sources at near infrared wavelengths to detect water in fuel. Some systems are designed to have path lengths between the light source and detector on the order to centimeters to be suitable for detecting water. Such systems may be ineffective at distinguishing from dissolved water and water droplets, which may have different impacts on the injectors. Further, such system may provide inaccurate sizing information when multiple water droplets are present in the detector.

There is a need for improved sensors to mitigate fuel injector damage and to improve the performance of internal combustion engines over time.

SUMMARY

Various aspects of the present disclosure relate to droplet sensors configured to detect liquid in a different fluid using a sensing channel, such as detecting liquid droplets dispersed in a different fluid using a microfluidic channel. In some embodiments, the droplet detection sensors may be configured to detect water droplets dispersed in a hydrocarbon fluid, such as fuel, which may be described as a microfluidic water-in-fuel (WIF) sensor. Infrared light may be used by the droplet sensors to measure light absorbance through the microfluidic channel and determine whether or how much of a liquid droplet is present in the fluid. The droplet sensor may be configured to differentiate, or distinguish, between liquid droplets dispersed in fluid and dissolved liquid in fluid as the fluid flows through the microfluidic channel. Information from the sensor may be used to determine one or more of the concentration of liquid in the fluid, the liquid droplet size, or the liquid droplet rate of flow through the microfluidic channel. A water level may also be measured using the sensor.

In one aspect, the present disclosure relates to a system including a microfluidic channel configured to receive a flow of a first fluid and a second fluid dispersed in the first fluid. The second fluid has a different composition than the first fluid. The system also includes a light source configured to direct a light beam in a frequency band along a path through the microfluidic channel. The frequency band is selected to have a higher absorbance by the second fluid than by the first fluid. The system further includes an aperture element defining a light aperture positioned in the path of the light beam from the light source. The system further includes a light detector positioned to receive the light beam in a sensing area after passing through the microfluidic channel and the light aperture. The light detector is configured to provide a signal representing an amount of light in the frequency band that remains after passing through the microfluidic channel. The system further includes a controller operably coupled to the light detector and configured to determine whether the second fluid is in droplet form based on the signal.

In another aspect, the present disclosure relates to a system including a fuel and water separator having a housing defining a water collection volume. The water collection volume is fluidly connected to an engine fuel line and fluidly connected to a water drain outlet. The system also includes a light source configured to direct a light beam in a frequency band along a path through the water collection volume. The frequency band is selected to be absorbed by water. The system further includes a light detector positioned to receive the light beam in a sensing area after passing through at least part of the water collection volume. The light detector is configured to provide a signal representing an amount of light in the frequency band. The system further includes a controller operably coupled to the light detector and configured to determine whether water is detected based on the signal.

In yet another aspect, the present disclosure relates to a system including a microfluidic channel configured to receive a flow of hydrocarbon fluid. The microfluidic channel has a cross-sectional area sized to receive one water droplet at a time when a water droplet of a predetermined size is dispersed in the hydrocarbon fluid. The system also includes a light source positioned outside the microfluidic channel configured to generate light in a selected frequency band such that the water droplet has a higher absorbance than the hydrocarbon fluid in the selected frequency band. The system further includes a light detector sensitive to the selected frequency band positioned outside the microfluidic channel and configured to provide a signal representing an amount of light remaining after passing through the microfluidic channel. The system additionally includes a light aperture positioned between the light source and the light detector, wherein light from the light source passing through the light aperture forms a light beam defining a beam axis that extends through the light source, the microfluidic channel, and the light detector. The system still further includes a controller operably connected to the light detector and configured to detect one or more water droplets dispersed in the flow of hydrocarbon fluid based on the signal from the light detector representing the amount of light from the light source remaining after passing through the microfluidic channel and the light aperture.

In still another aspect, the present disclosure relates to a sensor including a microfluidic channel sized to receive a flow of fluid. The microfluidic channel has a cross-sectional area sized to receive one liquid droplet at a time when a liquid droplet of a predetermined size is dispersed in the fluid. The sensor also includes a light source positioned outside the microfluidic channel configured to generate light in a selected frequency band such that the droplets have a different absorbance than the different liquid in the selected frequency band. The sensor further includes a light detector sensitive to the selected frequency band positioned outside the microfluidic channel and configured to provide a signal representing an amount of light remaining after passing through the microfluidic channel. The sensor additionally includes a light aperture positioned between the light source and the light detector, wherein light from the light source passing through the light aperture forms a light beam defining a beam axis that extends through the light source, the microfluidic channel, and the light detector. A width of the light aperture and the light detector define a sensing area. The sensor still further includes a controller operably connected to the light detector and configured to determine a droplet rate through the sensing area of the microfluidic channel based on the signal from the light detector representing the amount of light from the light source remaining after passing through the microfluidic channel and the light aperture.

In a further aspect, the present disclosure relates to a water droplet sensor including a microfluidic channel defining a cross-sectional area less than 1 mm$^2$. The sensor also includes a light source positioned outside the microfluidic channel configured to generate light in a near infrared frequency band. The sensor further includes a light detector sensitive to the selected frequency band positioned outside the microfluidic channel and configured to provide a signal representing an amount of light remaining after passing through the microfluidic channel. The sensor additionally includes a light aperture positioned between the light source and the light detector, wherein light from the light source passing through the light aperture forms a light beam defining a beam axis that extends through the light source, the microfluidic channel, and the light detector. The aperture has a width less than 1 mm. The sensor still further includes a controller operably connected to the light detector and configured to detect one or more water droplets dispersed in the flow of hydrocarbon fluid based on the signal from the light detector representing the amount of light from the light source remaining after passing through the microfluidic channel and the light aperture.

BRIEF DESCRIPTION OF THE DRAWINGS

Various embodiments of the disclosure are illustrated in the drawings, which are summarized as follows:

FIG. 3A is a perspective view; FIG. 3B is a cross-sectional area view; FIG. 3C is a top-down view; and FIG. 3D is a light detector signal plot.

FIG. 4A is a perspective view; FIG. 4B is a cross-sectional area view; FIG. 4C is a top-down view; and FIG. 4D is a light detector signal plot.

FIG. 5A is a perspective view; FIG. 5B is a cross-sectional area view; FIG. 5C is a top-down view; and FIG. 5D is a light detector signal plot.

FIGS. 14A-B and 15A-B illustrate various droplet sensors that may be used in the system of FIG. 1 having a microfluidic channel submerged in a main flow channel.

DETAILED DESCRIPTION

Figure 1:
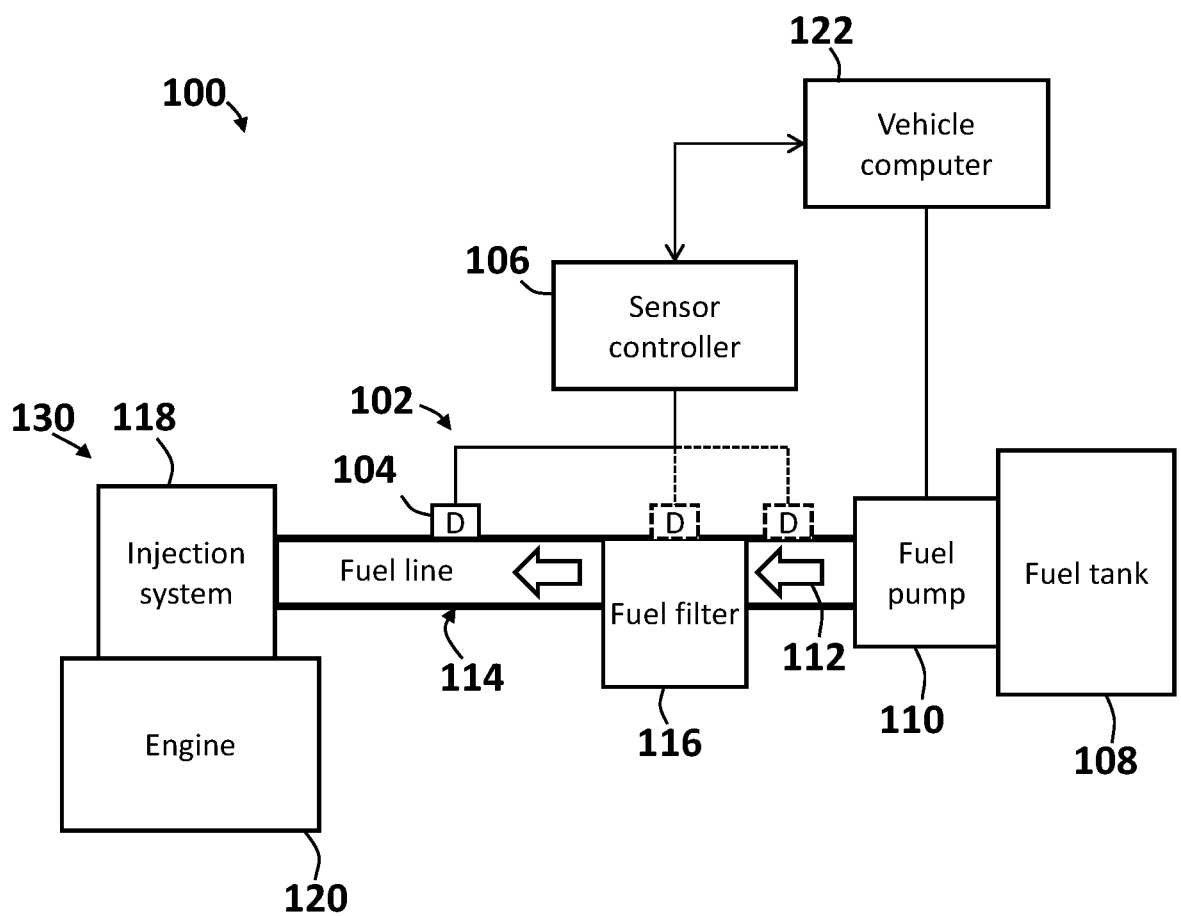
FIG. 1 illustrates an engine system with a droplet sensor according an embodiment of the present disclosure.

This disclosure relates to sensors configured to detect or characterize liquid droplets dispersed in a different fluid using one or more sensing channels, such as microfluidic channels. Although reference is made herein to water droplet sensors to protect engine fuel systems, such as water-in-fuel (WIF) sensors, the sensors and related techniques may be used to detect or characterize any liquid-in-fluid for which the absorbance of the liquid is different than the fluid, as well as various vehicular or non-vehicular applications. Non-limiting examples of other applications include detecting water-in-oil or detecting water in fuel tanks used for bulk fuel storage. A water level may also be measured using the sensor. Various other applications will become apparent to one skilled in the art having the benefit of this disclosure.

In applications related to engine fuel systems, different forms of water may have different effects on various components of the fuel system. For example, water that is not dissolved in the fuel, which may be described as free water, water droplets, or dispersed water, can cause damage to engine systems by causing rust, encouraging microbial growth, damaging fuel injectors, or causing poor ignition performance.

It may be beneficial to provide a sensor configured to precisely detect water droplets, or free water, instead of treating all forms of water equally. For example, the sensor may be substantially more sensitive to detecting water droplets, such as emulsified water in fuel, compared to dissolved water in fuel. It may be beneficial to provide sensors that may require less maintenance than existing sensors, such as float sensors or conductive WIF sensors. Further, it may be beneficial to provide a sensor that can be used to characterize the water droplets in the fuel.

The present disclosure provides droplet sensors that may be configured to use light, such as near infrared (NIR) wavelengths of light, to detect and size water droplets in a stream of hydrocarbon fluid, such as fuel or oil, using one or more microfluidic channels. The microfluidic channel may have a cross-sectional area that is a square, rectangle, circle, oval, half-circle, or any other suitable geometric shape. The microfluidic channel limits the path length of light across the channel that is used to detect water droplets in the fuel.

Advantageously, the limited path length provided by the microfluidic channel may reduce the occurrence of some water droplets being hidden behind other water droplets in a sensing area of the droplet sensor, thereby facilitating a sensitivity for detecting water droplets higher than for detecting dissolved water, which may facilitate accurate and precise characterization of the droplets.

In some applications, the width or depth of the microfluidic channel may be sized comparably to water droplets of interest. For example, droplets in a range from 15 up to 300 micrometers in diameter may be detected and sized using a microfluidic channel having a width of 150 micrometers. In other words, a droplet diameter down to one-tenth the width or depth of the microfluidic channel may be detected and sized. Smaller droplets may be detected and sized using a smaller channel, such as a width of 100 micrometers, a more precise alignment, or a more sensitive electronic detector.

The absorbance of water to NIR light may be substantially different than the absorbance of fuel. For example, water may have an absorbance greater than 3, whereas hydrocarbon fluid, such as fuel, may have an absorbance of less than 0.5 for a 10-millimeter path length. In one or more embodiments, a sensor includes an NIR light source centered at approximately 1550 nanometers, a circular aperture aligned with the channel, and a light detector. In some embodiments, the sensor may contain no focusing optics, and many parts of the droplet sensors, such as the light source and light detector, do not need to physically contact the water or fuel to detect water droplets using light, which may facilitate the robust operation of the sensor electronic, for example, due to less risk for corrosion compared to a conductive WIF sensor. In some embodiments, only the microfluidic channel may contact the water or fuel. Further, the droplet sensor may be designed using low-power usage parts and without moving parts, which may facilitate fewer maintenance events and longer operational times.

As used herein, the term "light" refers to energy at one or more wavelengths in the electromagnetic spectrum. Non-limiting examples of "light" include solar energy, infrared (IR) light, visible light, or ultraviolet (UV) light. Infrared light may include wavelengths in a range from 0.75 micrometers up to 1000 micrometers.

As used herein, the term "near infrared" or "NIR" light includes wavelengths greater than or equal to 0.75 or 0.78 micrometers and less than or equal to 2.5 or 3 micrometers.

As used herein, the term "or" is generally employed in its inclusive sense, for example, to mean "and/or" unless the context clearly dictates otherwise. The term "and/or" means one or all the listed elements or a combination of at least two of the listed elements.

Reference will now be made to the drawings, which depict one or more aspects described in this disclosure. However, it will be understood that other aspects not depicted in the drawings fall within the scope of this disclosure. Like numbers used in the figures refer to like components, steps and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows system 100 with droplet sensor 102 that is configured to detect liquid dispersed in a different fluid. In the illustrated embodiment, system 100 is an engine system including engine 120, fuel system 130, and computer 122.

Engine 120 may be an internal combustion engine. Droplet sensor 102 may be configured to detect water droplets in fluid. The fluid may be hydrocarbon fluid, such as a fuel or oil. In the illustrated embodiment, the fluid is fuel 112. Non-limiting examples of fuel 112 include gasoline and diesel. Fuel 112 is stored and provided to engine 120 by fuel system 130. System 100 may be used on a vehicle for on-road or off-road applications, such as trucking or mining. In such applications, computer 122 may be a vehicle computer, such as an engine control module (ECM) or other on-board computer.

As illustrated, fuel system 130 includes droplet sensor 102, fuel tank 108, fuel pump 110, fuel line 114, fuel filter 116, and injection system 118. Fuel tank 108 is in fluid communication with fuel pump 110, fuel line 114, and injection system 118. Fuel 112 is stored in fuel tank 108 and pumped by fuel pump 110 when system 100 is in operation combusting fuel 112 in engine 120. Fuel pump 110 is configured to provide a flow of fuel 112, or fuel flow, to one or more fuel injectors of injection system 118. Fuel line 114 is configured to deliver fluid to injection system 118. Fuel 112 enters fuel line 114 at fuel pump 110 and exists fuel line 114 at injection system 118. Injection system 118 may include a pressurized fuel rail and one or more fuel injectors. Injection system 118 is configured to provide a pressurized spray of fuel 112 into one or more combustion cylinders of engine 120.

Fuel filter 116 is positioned, or disposed, along fuel line 114. Fuel 112 may contain water. Fuel filter 116 is configured to remove water from fuel 112. Fuel filter 116 may be a fuel-water separator (FWS), for example, as used in some on-vehicle diesel engine systems. Water in fuel 112 may cause damage to various components of system 100. For example, water may cause damage to one or more injectors of injection system 118. In particular, water droplets in fuel 112 may cause damage to one or more injectors of injection system 118 when vaporized in the combustion cylinder. Dissolved water in fuel 112 may not cause similar damage.

Droplet sensor 102 may be positioned, or disposed, along fuel line 114 to detect water in fuel 112. Droplet sensor 102 may be configured to be more sensitive to detecting water droplets in fuel 112 than dissolved water in fuel 112 to provide reliable indication of potential damage to any injectors of injection system 118.

Droplet sensor 102 includes one or more detection assemblies 104. Each detection assembly 104 may be configured to receive a flow of fuel 112 for measuring water droplets. Fuel 112 from fuel line 114 may flow through each detection assembly 104. Fuel 112 may be returned to fuel line 114 after measurement. Fuel 112 may enter each using the flow of fuel 112 through fuel line 114 provided by fuel pump 110. In other words, fuel 112 may enter some or all detection assemblies 104 passively.

In some embodiments, droplet sensor 102 may include one or more separate pumps (not shown), different than fuel pump 110, to actively provide a flow of fuel 112 from fuel line 114 to some or all detection assemblies 104. The separate pumps, or sampling pumps, may be positioned downstream of any sensing channel or microfluidic channel so that the pump does not affect measurement of droplets. For example, a pump may have the effect of "chopping up" some water droplets.

As used herein, the term "downstream" refers to a direction along fuel line 114 toward fuel pump 110. The term "upstream" refers to the opposite of downstream, or a direction along fuel line 114 toward injection system 118.

In the illustrated embodiment, fuel pump 110 is positioned upstream of fuel filter 116. In other embodiments (not shown), fuel filter 116 is positioned upstream of fuel pump 110. In some embodiments (not shown), system 100 includes two or more fuel filters 116. For example, one fuel filter 116 may be positioned upstream and one fuel filter 116 may be positioned downstream of fuel pump 110. Each fuel filter 116 may be the same or different. In some embodiments, water may be removed from fuel at the upstream fuel filter 116, the downstream fuel filter 116, or both.

Each detection assembly 104 may include a microfluidic channel configured to receive a flow of fuel 112 from fuel line 114. Each microfluidic channel may be positioned adjacent or proximate to a main flow of fuel 112 along fuel line 114. In some embodiments, some or all microfluidic channels of detection assembly 104 are in parallel fluid communication with fuel line 114. In some embodiments, some or all microfluidic channels of detection assembly 104 are disposed in the main flow of fuel line 114, such that some of or all the main flow is directed through one or more microfluidic channels.

Depending on the application, droplet sensor 102 may be positioned at one or more locations along fuel line 114, such as upstream, downstream, or at the location of fuel filter 116. In some embodiments (not shown), droplet sensor 102 is located on a fuel return line (not shown) in fluid communication between injection system 118 and fuel tank 108. In some embodiments (not shown), droplet sensor 102 may be built into, or integrated with, one or more injectors of injection system 118. In other words, the droplet sensor 102 may be directly integrated into the fuel injector or the injection system 118.

In one embodiment, droplet sensor 102 includes one detection assembly 104. The one detection assembly 104 may be positioned downstream of fuel filter 116. Alternatively, the one detection assembly 104 may be positioned at fuel filter 116 or upstream of fuel filter 116. In some embodiments, droplet sensor 102 includes a combination of detection assemblies 104 positioned at one or more locations selected from upstream, downstream, or at the location of fuel filter 116. One or more detection assemblies 104 may be positioned at the same location along fuel line 114.

Positioning detection assembly 104 downstream of, or at, fuel filter 116 may be used to provide information used to determine the quality of water-fuel separation by fuel filter 116, which may be used to indicate that fuel filter 116 is operating correctly or may need maintenance or replacement. Positioning detection assembly 104 upstream of, or at, fuel filter 116 may be used to provide information used to determine the quality of fuel 112 stored in fuel tank 108 or being provided along fuel line 114, which may be used to indicate that fuel tank 108 is operating correctly or may need maintenance or replacement or that fuel 112 provided to fuel tank 108.

As fuel 112 approaches injection system 118, fuel 112 may reach a high temperature, for example, due to the proximity to injection system 118 or engine 120. In some embodiments, detection assembly 104 may be positioned upstream from injection system 118 a sufficient distance to prevent the high temperature of some injection systems from substantially impacting the performance of certain droplet sensors 102.

Droplet sensor 102 may include sensor controller 106. Sensor controller 106 may be operably connected, or coupled, to one or more detection assemblies 104. Each detection assembly 104 may make measurements and provide information characterizing water droplets detected in fuel 112 to sensor controller 106. Information may be provided in the form of a signal, such as an electrical signal. Examples of electrical signals include a current signal, voltage signal, and power signal. Information from detection assemblies 104 may be used by sensor controller 106 to determine various characteristics corresponding to the water droplets in fuel 112, such as droplet size, droplet rate, or the amount of water in fuel 112 (for example, a concentration).

Sensor controller 106 may be operably connected to computer 122. Computer 122 may be used to control various aspects of fuel system 130, such as flow rate of fuel 112 or injection timing for injection system 118. Sensor controller 106 and computer 122 are part of a control system of system 100 and may be separate components. In some embodiments, the functionality of sensor controller 106 and computer 122 may be integrated into a single component, such as a single controller or computer.

Droplet sensor 102 may be configured to detect a predetermined size of liquid droplet, or droplet size. As used herein, "droplet size" may be described interchangeably using a volume or using a spherical diameter corresponding to the volume of a liquid droplet when shaped as a sphere. In other words, the volume of a liquid droplet of any shape may be described by a spherical diameter of the same droplet when re-shaped into a sphere. In this manner, droplet size may be described as a volume corresponding to a specified spherical diameter.

In some embodiments, droplet sensor 102 is configured to detect or characterize a droplet size greater than or equal to 5, 10, 15, 50, 100, 150, 250, 300, or 1000 micrometers. In some embodiments, droplet sensor 102 is configured to detect or characterize a droplet size less than or equal to 5000, 1000, 300, 250, 150, or 100 micrometers. In some embodiments, droplet sensor 102 is configured to detect or characterize a droplet size in a range from 5 up to 5000 micrometers. In one or more embodiments, droplet sensor 102 is configured to detect or characterize a droplet size in a range from 10 to 300 micrometers.

In fuel system applications, droplet sizes less than 10 micrometers may not be considered liquid droplets that negatively impact the operation of injection system 118 of system 100. In particular, such water droplet sizes may be considered unstable below 10 micrometers and may not substantially contribute to damaging fuel injectors. Further, water in fuel that passes through typical fuel pumps 110 tend to form droplets of at least about 10 micrometers.

In general, one or more of the components, such as controllers, sensors, detectors, or computers, described herein may include a processor, such as a central processing unit (CPU), computer, logic array, or other device capable of directing data coming into or out of the sensor. The controller may include one or more computing devices having memory (which may include storage drives), processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

Figure 2:
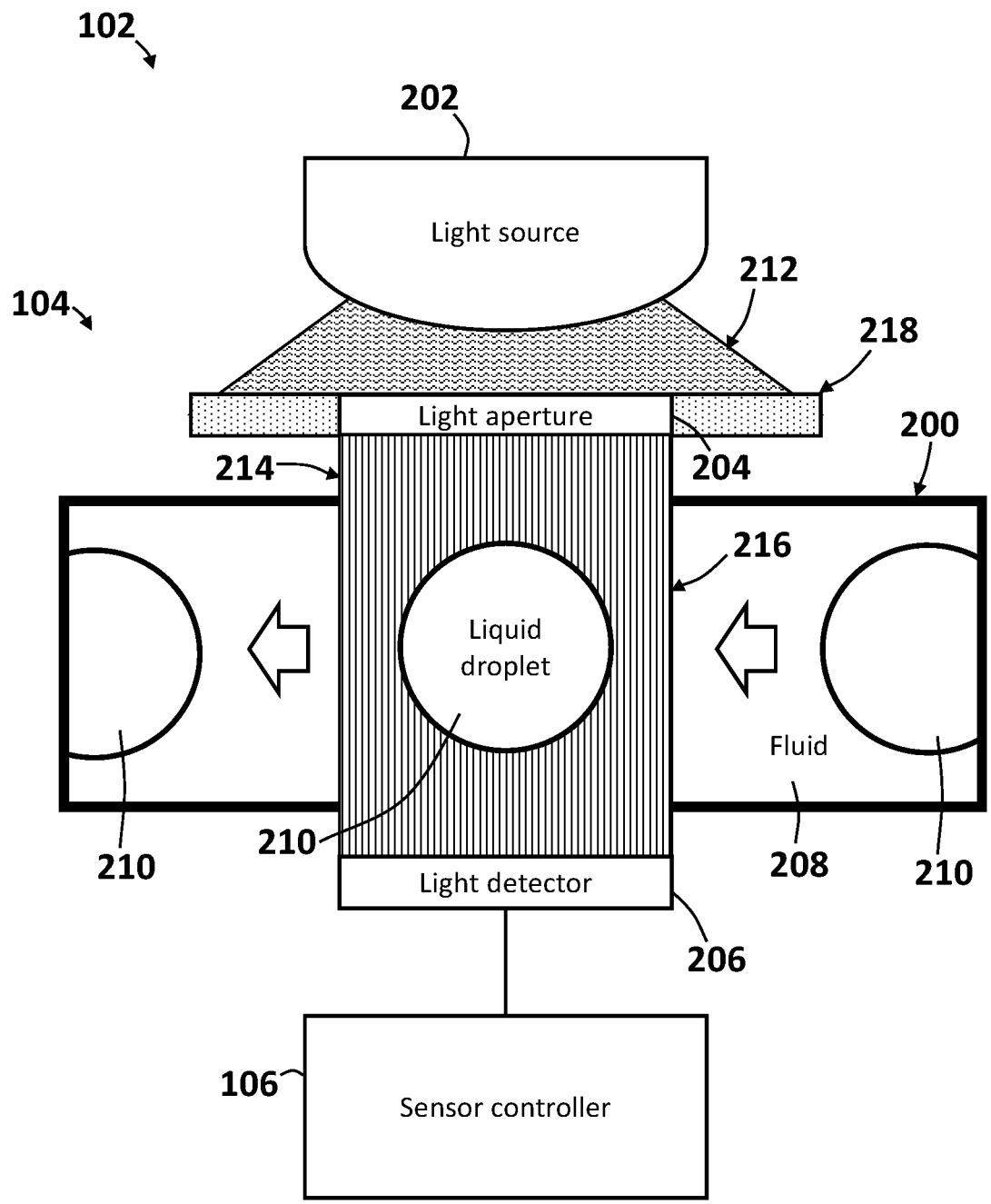
FIG. 2 illustrates a droplet sensor that may be used in the system of FIG. 1.

FIG. 2 shows various components of droplet sensor 102 including detection assembly 104 and sensor controller 106 that may be used with system 100 of FIG. 1. In the illustrated embodiment, detection assembly 104 includes microfluidic channel 200, light source 202, light aperture 204, and light detector 206. Sensor controller 106 is operably connected to light detector 206 and may also be operably connected to light source 202.

Microfluidic channel 200 is configured to receive a flow of fluid 208. Microfluidic channel 200 may include an inlet to receive the flow of fluid 208 and an outlet to discharge the flow of fluid 208. The droplet sensor 102 may be configured to detect and characterize liquid droplets 210 in the flow of fluid 208 may also flow through microfluidic channel 200 in a forward direction toward the outlet or even in reverse direction toward the inlet.

Liquid droplets 210 may be dispersed in fluid 208 in microfluidic channel 200. For example, liquid droplets 210 may be suspended in fluid 208 in a separate phase. In other words, liquid droplets 210 are not dissolved in fluid 208.

In general, microfluidic channel 200 is sized to receive one or more liquid droplets 210 at a time. In some embodiments, microfluidic channel 200 has a cross-sectional area sized to receive one liquid droplet 210 of a predetermined size at a time. In particular, the cross-sectional area of microfluidic channel 200 may be about the same size as a cross-sectional area of liquid droplet 210, which may facilitate counting one liquid droplet 210 at a time to facilitate accurate counting and sizing of liquid droplet 210.

The cross-sectional area may be defined orthogonal to the direction of the flow of fluid 208. In other words, the cross-sectional area may be described as transverse to a longitudinal flow of fluid 208. In some embodiments, microfluidic channel 200 has a cross-sectional area less than or equal to 1, 0.5, 0.2, 0.1, 0.05, 0.04, 0.03, or 0.02 mm$^2$. In some embodiments, microfluidic channel 200 has a cross-sectional area greater than or equal to 0.01, 0.02, 0.03, 0.04, 0.05, 0.1, 0.2, or 0.5 mm$^2$. For example, the cross-sectional area of a 150×150-micrometer microfluidic channel 200 would be 0.0225 mm$^2$.

Cross-sectional area may be defined as a channel depth multiplied by a channel width. Both channel depth and channel width may be orthogonal to the direction of the flow of fluid 208. In some embodiments, the channel depth is less than or equal to the channel width. Using a shallow channel depth may prevent liquid droplets 210 from stacking, or hiding behind one another, as the liquid droplets flow through microfluidic channel 200.

In some embodiments, the channel width is less than or equal to 5000, 2000, 1000, 500, 300, 250, 200, 150, or 100 micrometers. In some embodiments, the channel width is greater than or equal to 50, 100, 150, 200, 250, 300, 500, 1000, or 2500 micrometers. In one or more embodiments, the channel width is 150 micrometers. In one or more embodiments, the channel width is 250 micrometers.

In some embodiments, the channel depth is less than or equal to 750, 500, 300, 250, 200, 150, 120, or 100 micrometers. In some embodiments, the channel depth is greater than or equal to 50, 100, 120, 150, 200, 250, 300, or 500 micrometers. In one or more embodiments, the channel depth is less than or equal to 150 micrometers. In one or more embodiments, the channel depth is less than or equal to 250 micrometers.

In the illustrated embodiment, light source 202 is positioned outside microfluidic channel 200. Light aperture 204 is positioned between light source 202 and light detector 206. In some embodiments, light aperture 204 is positioned before microfluidic channel 200, for example, between light source 202 and microfluidic channel 200. In some embodiments, light aperture 204 is positioned after microfluidic channel 200, for example, between microfluidic channel 200 and light detector 206.

Light source 202 is configured to direct light 212 through light aperture 204 to form light beam 214. Light beam 214 is directed to pass through microfluidic channel 200. Light beam 214 may be collimated or substantially collimated by light aperture 204, at least for the path length of light beam 214 through microfluidic channel 200. Light beam 214 may define a beam axis extending through the microfluidic channel 200. The walls of microfluidic channel 200 may be formed of a light transparent material, at least to light 212 provided by light source 202. The path of light beam 214 intersecting with microfluidic channel 200 defines sensing area 216, which may also be described as a sensing volume, in which liquid droplets 210 may be detected. After light beam 214 passes through microfluidic channel 200, light beam 214 is received by light detector 206, which is positioned outside of microfluidic channel 200 in the illustrated embodiment. When liquid droplet 210 and fluid 208 are in sensing area 216, light detector 206 may be used to determine an absorbance of light beam 214 by liquid droplet 210 and fluid 208 to detect, size, or otherwise characterize liquid droplet 210.

As used herein, the term "path length" refers to the distance that light from light source 202 travels in fluid to be measured. In some embodiments, the path length may be equal to a width or depth of microfluidic channel 200. The path length may be small to improve sensitivity to liquid droplets 210. In some embodiments, the path length is less than or equal to 2000, 1000, 500, 300, 250, 200, 150, or 100 micrometers. In one or more embodiments, the path length is less than or equal to 1000 micrometers.

Light source 202 is configured to generate light in a selected frequency band such that liquid droplet 210 has a different absorbance than fluid 208 in the selected frequency band. In one or more embodiments, liquid droplet 210 has a higher absorbance than fluid 208 when the liquid is water and fluid 208 is a hydrocarbon fluid. In fuel system applications, for example, light source 202 may generate light 212 in at least the NIR frequency band. In some embodiments, NIR light 212 may include an emission peak in, or at least include frequencies in, a range from 1400 to 1600 nanometers. In particular, NIR light 212 may include an emission peak centered at or near 1550 nanometers. In some embodiments, NIR light 212 may include an emission peak in, or at least include frequencies in, a range from least 900 to 1100 nanometers. In particular, NIR light 212 may include an emission peak centered at or near 1000 nanometers.

Light source 202 may include any suitable type of light source capable of providing light 212 in a selected frequency band. In some embodiments, light source 202 is a light-emitting diode (LED). The LED light source 202 may be a low-power LED. In some embodiments, the LED light source emit omnidirectionally or in all directions from the light-emitting junction. In some embodiments, the LED light source emits primarily in one direction. In some embodiments, light source 202 may be paired with or include a fiber optic cable that directs light to microfluidic channel 200. Light aperture 204 may be used to allow a narrow light beam 214 through microfluidic channel 200, which may facilitate eliminating noise or false signals, for example, due to scattering and reflectance.

Light aperture 204 includes an opening in an aperture element 218. As used herein, "aperture" refers to the opening, or void, within the aperture element. Light aperture 204 has a width that is sized relative to microfluidic channel 200 and light detector 206 to facilitate optimal sensitivity for detecting liquid droplets 210 in fluid 208. In some embodiments, the width of light aperture 204 is the same or substantially the same as the channel width of microfluidic channel 200.

Additionally, or alternatively, light aperture 204 may be sized relative to a predetermined droplet size of interest. For example, in some embodiments, the width of light aperture 204 may be designed to be less than or equal to 2, 3, 4, 5, 6, 7, 8, 9, or 10 times the droplet size of interest. In some embodiments, the width of light aperture 204 may be designed to be greater than or equal to 1, 2, 3, 4, 5, 6, 7, 8, or 9 times the droplet size of interest.

Light aperture 204 may have any suitable geometric shape. In some embodiments, light aperture 204 has a round or circular shape, such as a circle or oval. In some embodiments, light aperture 204 has a polygonal shape, such as a triangle, square, trapezoid, or rectangle. Light aperture 204 may have a length, which may extend along the same direction as the flow of fluid 208. In one or more embodiments, the length of light aperture 204 may be the same or substantially the same as the width of light aperture 204.

In some embodiments, light aperture 204 has a width less than or equal to 5000, 2000, 1000, 500, 300, 250, 200, 150, or 100 micrometers. In some embodiments, the width of light aperture 204 is greater than or equal to 50, 100, 150, 200, 250, 300, 500, 1000, or 2500 micrometers. In one or more embodiments, the width of light aperture 204 is 150 micrometers. In one or more embodiments, the width of light aperture 204 is 250 micrometers.

Light detector 206 may be any suitable type of photodetector sensitive to the selected frequency band, which may be an NIR frequency band. Light detector 206 is also configured to provide a signal representing an amount of light from light beam 214 remaining after passing through microfluidic channel 200. In particular, light detector 206 may be configured to generate an electrical signal, such as a current, voltage, or power signal, in response to receiving light in the selected frequency band. Non-limiting examples of types of photodetectors include indium-gallium-arsenide (InGaAs) or germanium (Ge) photodiodes. For example, an InGaAs photodiode may be sensitive to light 212 in a frequency band from 1100 to 1700 nanometers. A Ge photodiode may have a peak sensitivity at 1550 nanometers.

Sensor controller 106 is configured to detect, size, or otherwise characterize one or more liquid droplets 210 dispersed in the flow of fluid 208 based on the signal from light detector 206. In some embodiments, sensor controller 106 may be configured to detect one liquid droplet 210 at a time dispersed in the flow of fluid 208, particularly liquid droplets 210 of a predetermined size. The signal may be used to determine an amount of liquid (e.g., water) per unit volume of fluid 208 (e.g., hydrocarbon fluid) excluding liquid dissolved in fluid 208.

In some embodiments, sensor controller 106 is configured to determine a droplet rate through sensing area 216. For example, a change in absorbance detected based on the signal from light detector 206 may indicate that liquid droplet 210 is entering or is leaving sensing area 216. Alternatively, or additionally, sensor controller 106 may be configured to determine a droplet size. In some embodiments, sensor controller 106 may determine a droplet rate or a droplet size based on at least one of: a magnitude of a pulse contained within the signal, a width of a pulse contained within the signal, a first threshold signal level for detecting a minimum size droplet in the sensing area, a second threshold signal level for detecting a droplet that fills the sensing area, and a threshold signal level crossing rate, which are described herein in more detail with respect to FIGS. 3-5. Sensor controller 106 may determine an amount of liquid 210 in droplet form per unit volume of fluid 208, such as a droplet concentration, based on droplet rate, droplet size, or both. In some applications, such as non-engine applications, when a droplet rate is regular or substantially regular, the droplet rate may be used to estimate or determine a droplet size or concentration.

In fuel systems applications, sensor controller 106 may be configured to provide a maintenance signal in response to detecting water in fuel. For example, a maintenance signal may be provided under certain conditions, such as when detecting a droplet above a threshold size, detecting a number of droplets above a threshold size, detecting a threshold number of droplets, determining a threshold volume of water based on detected droplets, detecting a threshold rate (or frequency) of droplets, or detecting a threshold concentration of water in fuel. These conditions may also be used for other liquid droplets in fluid.

FIGS. 3A-5D show various sizes of liquid droplets 303, 304, 305 that may be detected using a single microfluidic channel in detection assembly 104 of FIG. 2. In particular, FIGS. 3A-D are various illustrations showing when liquid droplet 303 with a large droplet size (e.g., a plug shape) greater than channel width 310 of microfluidic channel 312 flows through sensing area 314. FIGS. 4A-D are various illustrations showing when liquid droplet 304 with a medium droplet size (e.g., a spherical shape) equal to channel width 310 flows through sensing area 314. FIGS. 5A-D are various illustrations showing when liquid droplet 305 with a small droplet size (e.g., a small spherical shape) less than channel width 310 flows through sensing area 314.

In the illustrated embodiments, channel depth 316 of the cross-sectional area 318 of microfluidic channel 312 is equal to channel width 310. In other words, microfluidic channel 312 has a square shaped cross-sectional area 318. Also, in the illustrated embodiments, sensing area 314 is in the shape of a cylinder, which may be provided by a light aperture in the shape of a circle. As described herein, various characteristics of liquid droplets 303, 304, 305 may be determined based on signals 323, 324, 325 detected, for example, in response to various liquid droplets 303, 304, 305.

As used herein, a "plug shape" may be used to describe a liquid droplet that has been squeezed into a microfluidic channel and may have a shape similar to two spherical caps connected by a cylinder.

Figure 3A:
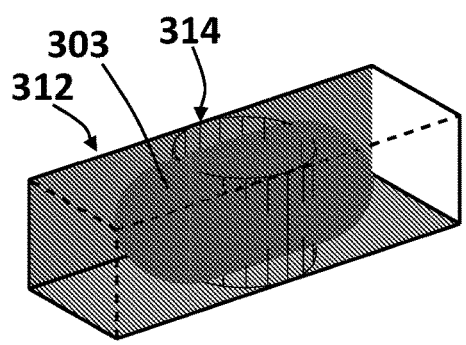
FIGS. 3A-D illustrate a large liquid droplet in a sensing area of a microfluidic channel of the droplet sensor of FIGS. 1-2.

FIG. 3A shows a snapshot of large liquid droplet 303 flowing through microfluidic channel 312 when a center of liquid droplet 303 is aligned with a center of sensing area 314 of microfluidic channel 312. FIG. 3B shows cross-sectional area 318 of microfluidic channel 312 at the center of sensing area 314 when liquid droplet 303 is positioned as shown in FIG. 3A. As can be seen, when liquid droplet 303 is constrained in microfluidic channel 312, width 333 of liquid droplet 303 is the same as channel width 310 and channel depth 316. When liquid droplet 303 is not constrained by microfluidic channel 312, liquid droplet 303 may have a spherical shape. For comparison, FIG. 3C shows a top-down view of liquid droplet 303 as visible in sensing area 314, also, when liquid droplet 303 is positioned as shown in FIG. 3A. As can be seen, liquid droplet 303 fills sensing area 314 as liquid droplet 303 flows through sensing area 314.

Figure 3D:
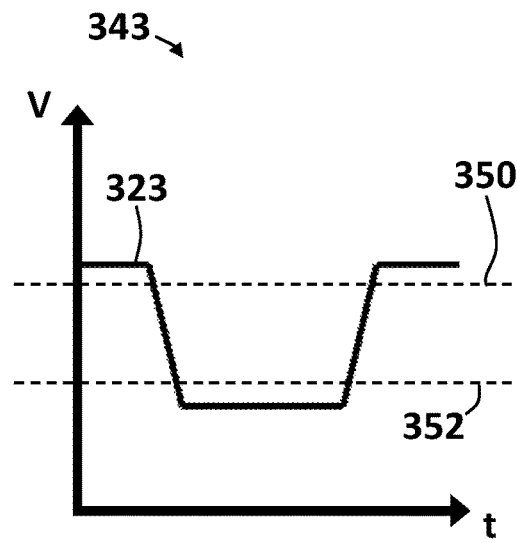
Figure 3B:
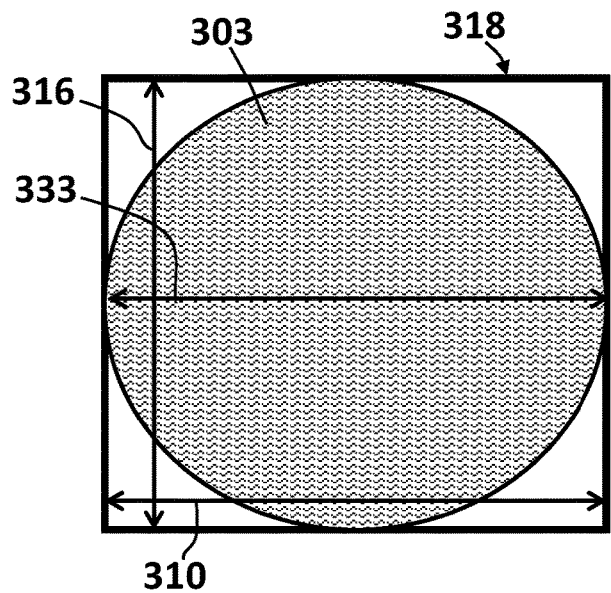
Figure 3C:
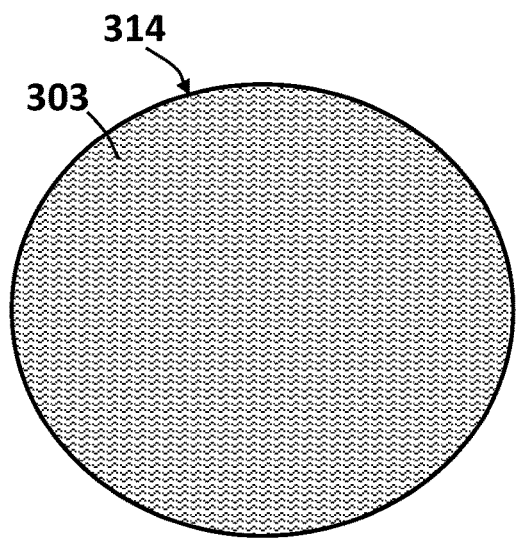

FIG. 3D shows plot 343 of one example of a signal from light detector 206 (FIG. 2). Plot 343 of signal 323 shows electrical voltage V versus time t. Signal 323 may be inversely related to absorbance of liquid in sensing area 314. In other words, as light-absorbing liquid enters sensing area 314, signal 323 may drop and, as light-absorbing liquid leaves sensing area 314, signal 323 may rise. In other embodiments, signal 323 may be directly related (e.g., the opposite to inversely related) to absorbance of liquid in sensing area 314, for example, depending on the particular type of light detector used.

Various thresholds may be used to characterize liquid droplet 303. In the illustrated embodiment, before liquid droplet 303 enters sensing area 314, signal 323 exceeds first threshold 350. As light-absorbing liquid droplet 303 begins to fill sensing area 314, signal 323 drops. After liquid droplet 303 completely fills sensing area 314, signal 323 falls below second threshold 352. As liquid droplet 303 begins to leave sensing area 314, signal 323 rises and exceeds second threshold 352. After liquid droplet 303 completely leaves sensing area 314 signal 323 may once again exceed first threshold 350.

Figure 4A:
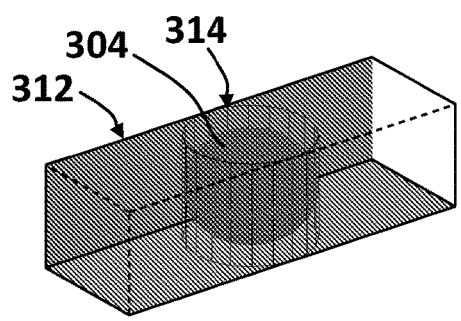
FIGS. 4A-D illustrate a medium liquid droplet in a sensing area of a microfluidic channel of the droplet sensor of FIGS. 1-2.

FIG. 4A shows a snapshot of medium liquid droplet 304 flowing through microfluidic channel 312 when a center of liquid droplet 304 is aligned with a center of sensing area 314 of microfluidic channel 312. FIG. 4B shows cross-sectional area 318 of microfluidic channel 312 at the center of sensing area 314 when liquid droplet 304 is positioned as shown in FIG. 4A. As can be seen, when liquid droplet 304 is in microfluidic channel 312, width 334 of liquid droplet 304 is the same as channel width 310 and channel depth 316. For comparison, FIG. 4C shows a top-down view of liquid droplet 304 as visible in sensing area 314, also, when liquid droplet 304 is positioned as shown in FIG. 4A. As can be seen, liquid droplet 304 fills sensing area 314 as liquid droplet 304 flows through sensing area 314. In other words, both the large droplet size of liquid droplet 303 (FIG. 3A) and the medium droplet size of liquid droplet 304 (FIG. 4A) entirely fill sensing area 314.

Figure 4D:
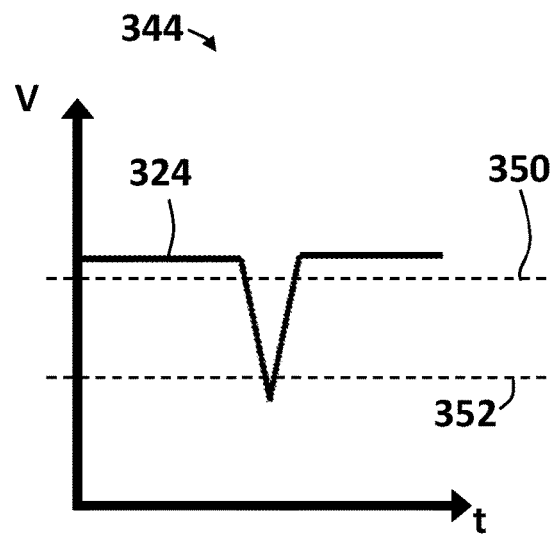
Figure 4B:
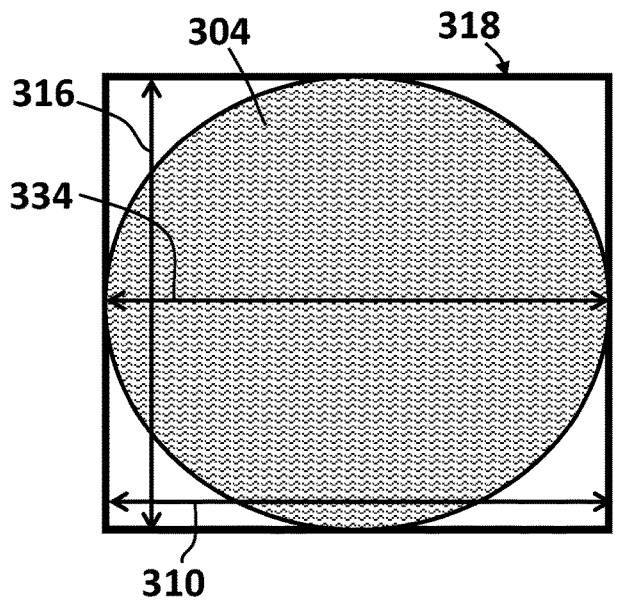
Figure 4C:
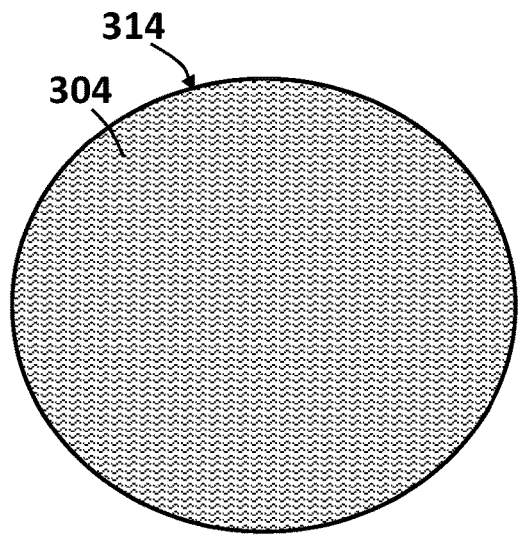

FIG. 4D shows plot 344 of signal 324 from light detector 206 (FIG. 2). Like FIG. 3D, plot 344 of signal 324 shows electrical voltage V versus time t. The same thresholds 350, 352 shown in FIG. 3D are shown here. In the illustrated embodiment, before liquid droplet 304 enters sensing area 314, signal 324 exceeds first threshold 350. As light-absorbing liquid droplet 304 begins to fill sensing area 314, signal 324 drops. Like FIG. 3D, after liquid droplet 304 completely fills sensing area 314, signal 324 falls below second threshold 352. As liquid droplet 304 begins to leave sensing area 314, signal 324 rises and exceeds second threshold 352. After liquid droplet 304 completely leaves sensing area 314 signal 324 may once again exceed first threshold 350. In contrast to FIG. 3D, the duration between signal 324 falling below second threshold 352 and subsequently exceeding second threshold 352 is substantially lower. As can be seen in FIG. 3D, the duration between crossings of second threshold 352 looks like a flat or substantially flat line, whereas signal 324 of FIG. 4D looks like a "V" or sharp valley. Further, the duration between signal 324 crossing first threshold 350 is shorter compared to signal 323 of FIG. 3D.

Figure 5A:
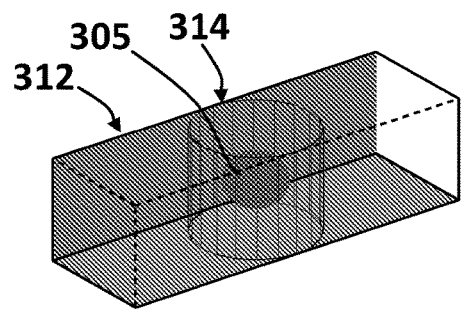
FIGS. 5A-D illustrate a small liquid droplet in a sensing area of a microfluidic channel of the droplet sensor of FIGS. 1-2.

FIG. 5A shows a snapshot of small liquid droplet 305 flowing through microfluidic channel 312 when a center of liquid droplet 305 is aligned with a center of sensing area 314 of microfluidic channel 312. FIG. 5B shows cross-sectional area 318 of microfluidic channel 312 at the center of sensing area 314 when liquid droplet 305 is positioned as shown in FIG. 5A. As can be seen, when liquid droplet 305 is in microfluidic channel 312, width 335 of liquid droplet 305 is less than channel width 310 and channel depth 316. For comparison, FIG. 5C shows a top-down view of liquid droplet 305 as visible in sensing area 314, also, when liquid droplet 305 is positioned as shown in FIG. 5A. As can be seen, liquid droplet 305 does not fill sensing area 314 as liquid droplet 305 flows through sensing area 314 in contrast to the large droplet size of liquid droplet 303 (FIG. 3A) and the medium droplet size of liquid droplet 304 (FIG. 4A).

Figure 5D:
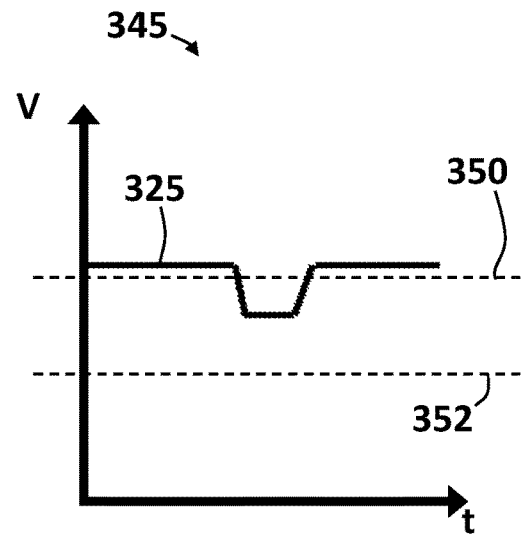
Figure 5B:
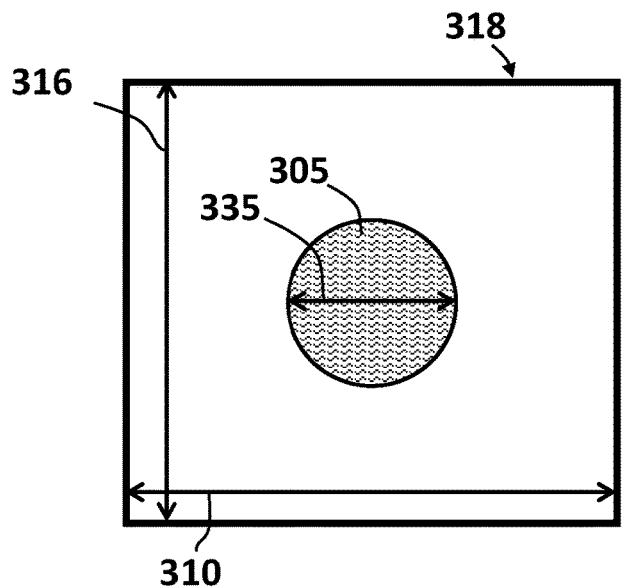
Figure 5C:
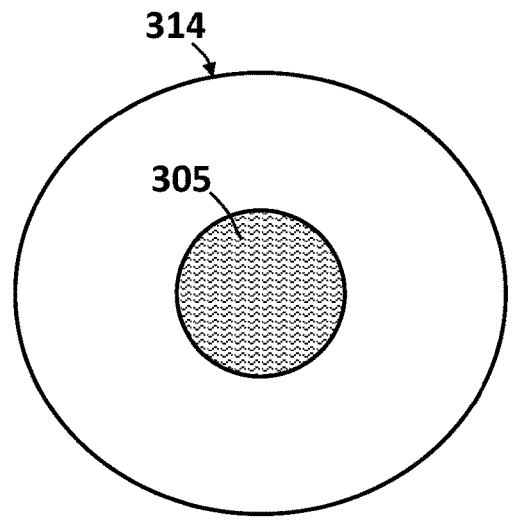

FIG. 5D shows plot 345 of signal 325 from light detector 206 (FIG. 2). Like FIGS. 3D and 4D, plot 345 of signal 325 shows electrical voltage V versus time t. The same thresholds 350, 352 shown in FIGS. 3D and 4D are shown here. In the illustrated embodiment, before liquid droplet 305 enters sensing area 314, signal 325 exceeds first threshold 350. As light-absorbing liquid droplet 305 begins to fill sensing area 314, signal 325 drops. In contrast to FIGS. 3D and 4D, after liquid droplet 305 completely enters sensing area 314, signal 325 does not fall below second threshold 352. As liquid droplet 305 begins to leave sensing area 314, signal 325 rises. After liquid droplet 305 completely leaves sensing area 314 signal 325 may once again exceed first threshold 350. In contrast to FIGS. 3D and 4D, signal 325 does not cross second threshold 352. Further, the duration between signal 325 crossing first threshold 350 is shorter compared to signal 323 of FIG. 3D and signal 324 of FIG. 4D. Signal 325 looks like a flat or substantially flat line when below first threshold 350, similar to FIG. 3D but unlike FIG. 4D. The flat line may be attributed to the length of liquid droplet 305 being shorter than the length of sensing area 314 such that the entire liquid droplet 305 is in sensing area 314 for a longer duration than as shown in FIG. 4D.

With reference to the various patterns observed in signals 323, 324, 325, various liquid droplets 303, 304, 305 may be identified and characterized. A droplet rate or droplet size may be determined based on a magnitude of a pulse contained within the signal from light detector 206 (FIG. 2). As used herein, the term "pulse" refers to a time when the signal falls below first threshold 350. A greater magnitude drop of the pulse may indicate a larger droplet size or slower droplet rate. Further, qualitatively, if the signal crosses first threshold 350 twice but does not cross second threshold 352 in between, then the droplet size may be determined as less than channel width 310. Vice versa, if the signal crosses second threshold 352 in between first threshold 350 crossings, then the droplet size may be qualitatively determined as at least the size of channel width 310.

In some embodiments, a droplet size may be determined based on the magnitude of the pulse contained within the signal when the signal level does not cross the second threshold. When the signal does not cross the second threshold, the droplet size may be determined to be less than channel width 310. In such cases, the droplet size may be determined based on the magnitude drop of the signal during the pulse. In general, the larger the magnitude drop, the larger the droplet size.

Additionally, or alternatively, a droplet rate or droplet size may be determined based on a width of a pulse contained within the signal from light detector 206. A greater width of the pulse, between first threshold 350 crossings, between second threshold 352 crossings, or both, may indicate a larger droplet size or slower droplet rate.

In some embodiments, a droplet size may be determined based on the width of the pulse contained within the signal when the signal level crosses the second threshold. When the signal crosses the second threshold, the droplet size may be determined to be at least the size of channel width 310. in such cases, the droplet size may be determined based on the time between crossings of the signal with one or both thresholds 350, 352, which may be used to indicate the width of the pulse. In general, the larger the width, the larger the droplet size.

First and second thresholds 350, 352 may be empirically determined and stored by sensor controller 106 (FIG. 2) for a particular application. A first threshold 350 may be set to detect a minimum size liquid droplet in sensing area 314. In general, the lower first threshold 350 is set, the larger the minimum size of liquid droplet detection. A second threshold 352 may be set to detect a liquid droplet that fills sensing area 314, such as liquid droplet 303 (FIG. 3A) or liquid droplet 304 (FIG. 4A), which may have a droplet size greater than or equal to channel width 310. A droplet rate or droplet size may be determined based on whether the signal crosses first threshold, second threshold, or both.

A droplet rate or droplet size may be determined based on a threshold signal level crossing rate, or how quickly the signal crosses first threshold 350, second threshold 352, or both. For example, the crossing of the signal from above to below first threshold 350 or second threshold 352 may be measured, or vice versa. In some embodiments, the crossing of the signal across one threshold 350, 352 may be used. For example, if the signal falls below first threshold 350, the next time the signal falls below first threshold 350, the signal must have risen above first threshold 350. Therefore, a droplet rate may be determined using only one type of threshold crossing.

In some embodiments of the present disclosure, more than one microfluidic channel may be used in a droplet sensor. For example, at least another microfluidic channel may be included in each detection assembly. The sensor controller operably connected to light detector 206 (FIG. 2) may be further configured to detect one or more liquid droplets dispersed in a flow of fluid through another microfluidic channel based on the signal from the light detector. The sensor controller may be configured to distinguish between liquid droplets flowing through each of the microfluidic channels.

Figure 6:
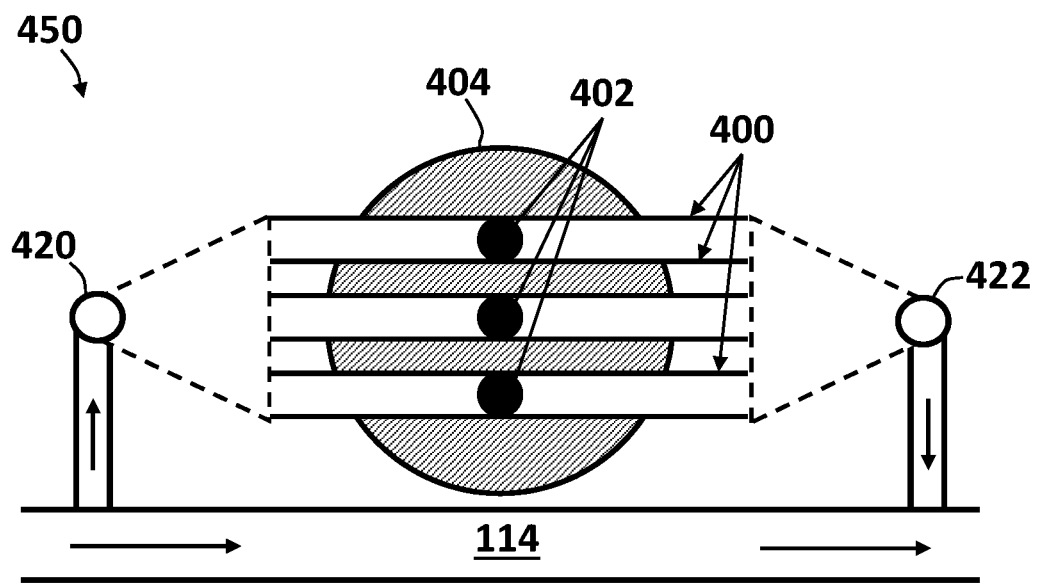
FIG. 6 illustrates a detection assembly that may be used in the system of FIG. 1.
Figure 7:
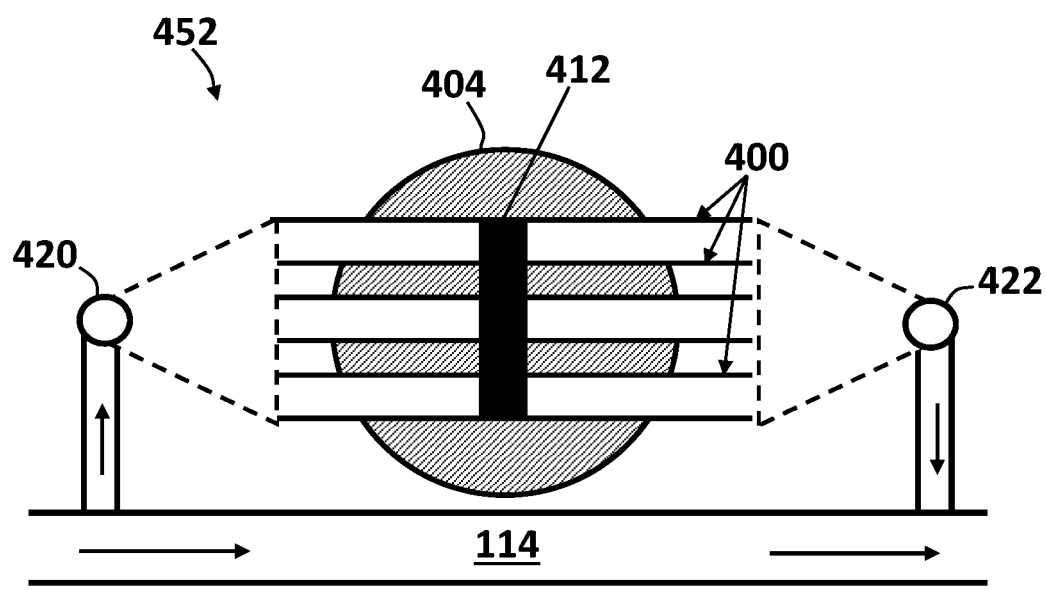
FIG. 7 illustrates another detection assembly that may be used in the system of FIG. 1.

FIGS. 6 and 7 show additional embodiments of detection assemblies 450, 452, which may be used with system 100 of FIG. 1. In the illustrated embodiments, each detection assembly 450, 452 includes a plurality of microfluidic channels 400. Each microfluidic channel 400 may share one inlet 420 and may share one outlet 422. The fluid connections between microfluidic channels 400, inlet 420, and outlet 422 are shown schematically with dashed lines. In some embodiments (not shown), microfluidic channels 400 may be in fluid communication with different inlets 420 and may be in fluid communication with different outlets 422. Inlet 420 and outlet 422 may be in fluid communication with a main fluid flow, for example, in fuel line 114 of system 100. As illustrated, microfluidic channels 400 are in parallel fluid communication with fuel line 114. Each detection assembly 450, 452 includes light detector 404 and an opposing light source (not shown). Microfluidic channels 400 may share one light detector 404 and one light source.

Each microfluidic channel 400 may have the same or different cross-sectional area. In some embodiments, the cross-sectional areas of each microfluidic channel 400 may be differently sized to detect different droplet sizes. Using a plurality of microfluidic channels 400 may be used in various applications to allow more fluid to be sampled at the same pressure drop compared to using a single microfluidic channel, allow a higher flowrate of fluid through the detection assembly, or lower the pressure drop for the same amount of fluid sampled. For example, using a plurality of microfluidic channels 400 may be used in-line with a main flow of fluid through fuel line 114.

Detection assembly 450 may include a plurality of light apertures 402. Each light aperture 402 corresponds to one microfluidic channel 400. Light apertures 402 may be used to define multiple light beams, which in turn define one sensing area per microfluidic channel 400. As liquid droplets flow through each microfluidic channel 400, light detector 404 will detect different levels of absorption corresponding to liquid droplets flowing through microfluidic channels 400. Light apertures 402 may have the same or different widths, which may facilitate sensitivity to the different droplet sizes. Each light aperture 402 may have any suitable shape, such as a circular shape.

Detection assembly 452 may include a single light aperture 412. Single light aperture 412 corresponds to the plurality of microfluidic channels 400. In other words, the plurality of microfluidic channels 400 share one light aperture 412. Light aperture 412 may have any suitable shape, such as a rectangular shape. In some embodiments (not shown), light aperture 412 may have different widths along each microfluidic channel 400.

In some embodiments (not shown), more than one light detector 404 may be used. For example, each microfluidic channel 400 may have a corresponding light detector. Each light detector may be operably connected to the same or a different sensor controller.

Figure 8:
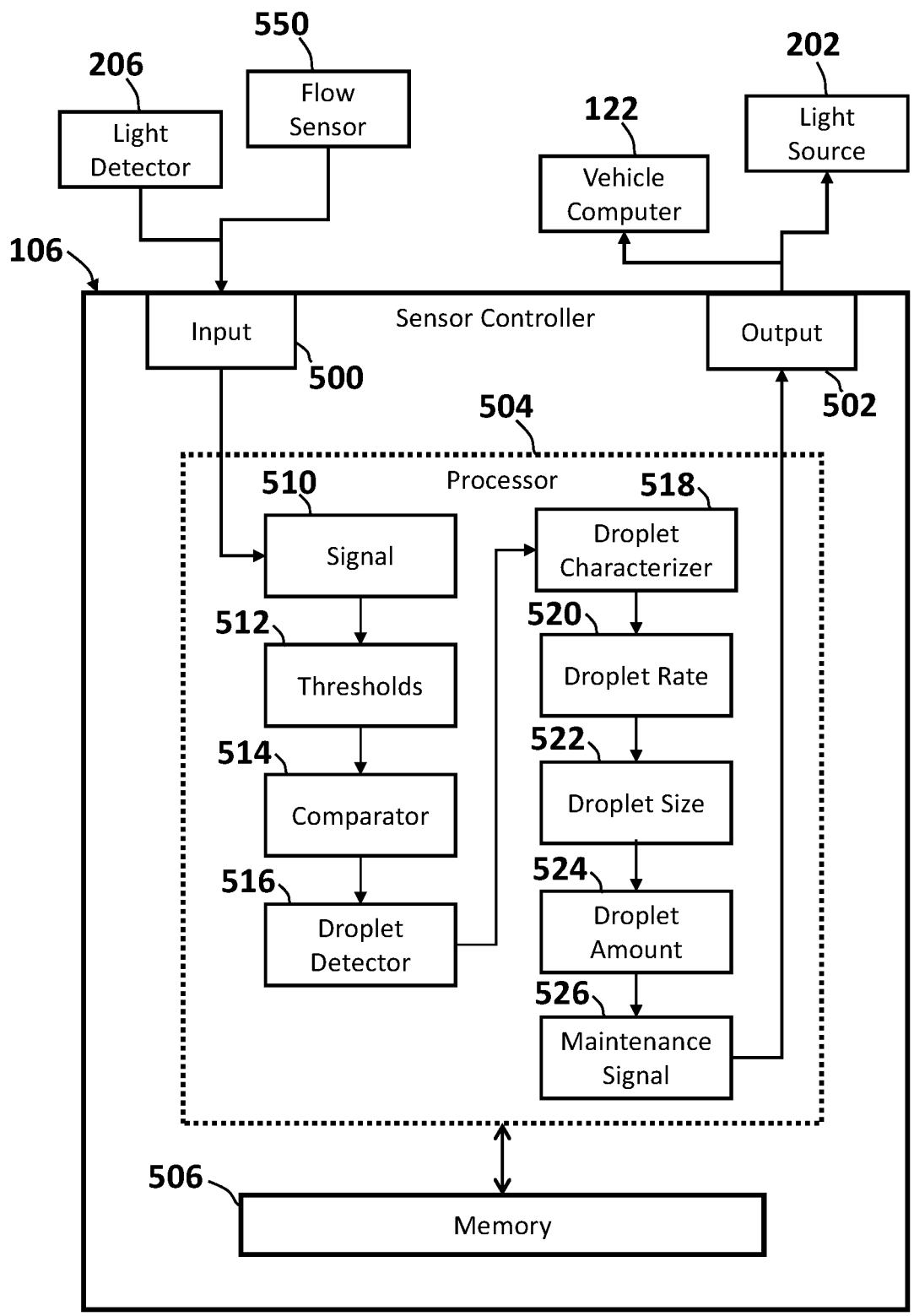
FIG. 8 illustrates a layout of a sensor controller that may be used in the system of FIG. 1.

FIG. 8 shows a layout of sensor controller 106 that may be used with droplet sensor 102 (FIGS. 1 and 2). As illustrated, sensor controller 106 includes input interface 500 and output interface 502. Sensor controller 106 may be operably connected to light detector 206 or optional flow sensor 550 using input interface 500. Sensor controller 106 may be operably connected to computer 122 or light source 202 using output interface 502. Each interface 500, 502 may be operably connected to processor 504, memory 506, or both. Processor 504 may be operably coupled to memory 506 to store and retrieve information or data, such as signal 510, threshold 512, droplet rate 520, droplet size 522, or droplet amount 524.

In the illustrated embodiment, processor 504 may be configured to receive signal 510 from light detector 206 using input interface 500. One or more thresholds 512 may be determined by processor 504 based on signal 510 or retrieved from memory 506. Various modules of processor 504 may be executed based on signal 510 and threshold 512. For example, signal 510 and threshold 512 may be compared using comparator 514 executed on processor 504. Based on the comparison, processor 504 may determine whether a liquid droplet has been detected using droplet detector 516. Further, various characteristics of the liquid droplet may be determined using droplet characterizer 518. Non-limiting examples of droplet characteristics that may be determined include droplet rate 520, droplet size 522, and droplet amount 524. In some embodiments, processor 504 may determine to provide a maintenance signal 526 to output interface 502.

A flow rate of fluid from flow sensor 550 may be used to determine some characteristics. In some embodiments, the flow meter or flow sensor 550 may be positioned in, upstream of, or downstream of the sensing channel or microfluidic channel. In general flow sensor 550 is positioned and configured to determine a flow rate of fluid through the microfluidic channel, which may also be described as a sensing channel.

Figure 9:
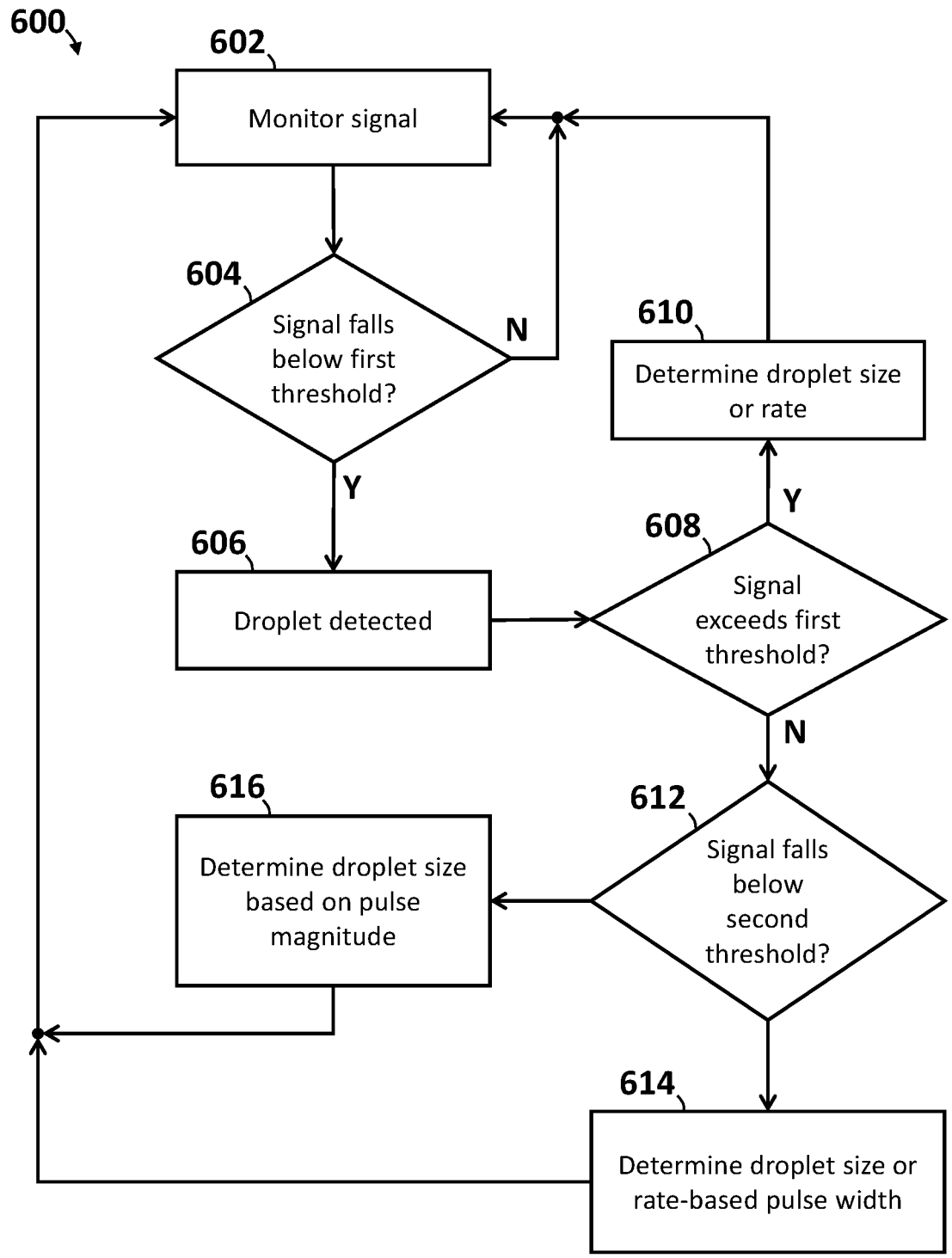
FIG. 9 illustrates a method of detecting and characterizing a liquid droplet that may be used with the system of FIG. 1.

FIG. 9 shows a flowchart describing method 600 that may be used with droplet sensor 102 of FIG. 2 or sensor controller 106 of FIG. 8. Method 600 may include monitoring a signal 602. If the monitored signal falls below a first threshold 604, method 600 may continue and determine that a liquid droplet has been detected 606. Otherwise, the signal may continue to be monitored 602.

After a droplet has been detected 606, if the signal exceeds the first threshold 608, for example, without falling below the second threshold, method 600 may continue and determine a droplet size or rate 610. For example, the droplet size may be determined to be less than a channel width of a microfluidic channel. As another example, a droplet rate may be determined based only on crosses of the first threshold. After the droplet size or rate is determined, the signal may continue to be monitored for another droplet 602. If the signal has not yet exceeded the first threshold 608, method 600 may continue and determine whether the signal has fallen below a second threshold 612.

If the signal falls below the second threshold 612, for example, before exceeding the first threshold, method 600 may determine droplet size or rate based on a pulse width 614. As described herein above, a signal below the second threshold may indicate that the droplet size is greater than or equal to the channel width of the microfluidic channel, and the pulse width may indicate the droplet size or rate. After determining droplet size or rate 614, the signal may continue to be monitored for another droplet 602.

Otherwise, if the signal does not fall below the second threshold 612, for example, before exceeding the first threshold, method 600 may determine droplet size based on a pulse magnitude 616. As described herein above, a signal above the second threshold may indicate that the droplet size is less than the channel width of the microfluidic channel, and the pulse magnitude may indicate the droplet size. After determining droplet size 616, the signal may continue to be monitored for another droplet 602.

The droplet sensor may be integrated with a main flow line in any suitable manner. Controlling piping dimensions (e.g., length or hydraulic diameter) and observing the impact of minor pressure head losses (e.g., expansions or contractions in hydraulic diameter) may allow pressure losses in the overall system to be controlled. In some cases, the droplet sensor may be integrated in a manner to reduce overall pressure or energy loss, for example, facilitating a shorter microfluidic channel length.

The microfluidic sensor may be in parallel fluid communication with a main flow branch. In some embodiments, the microfluidic channel may be configured to accept a bypass flow from the main flow. In some embodiments, the microfluidic channel may be at least partially disposed within the main flow.

Figure 10:
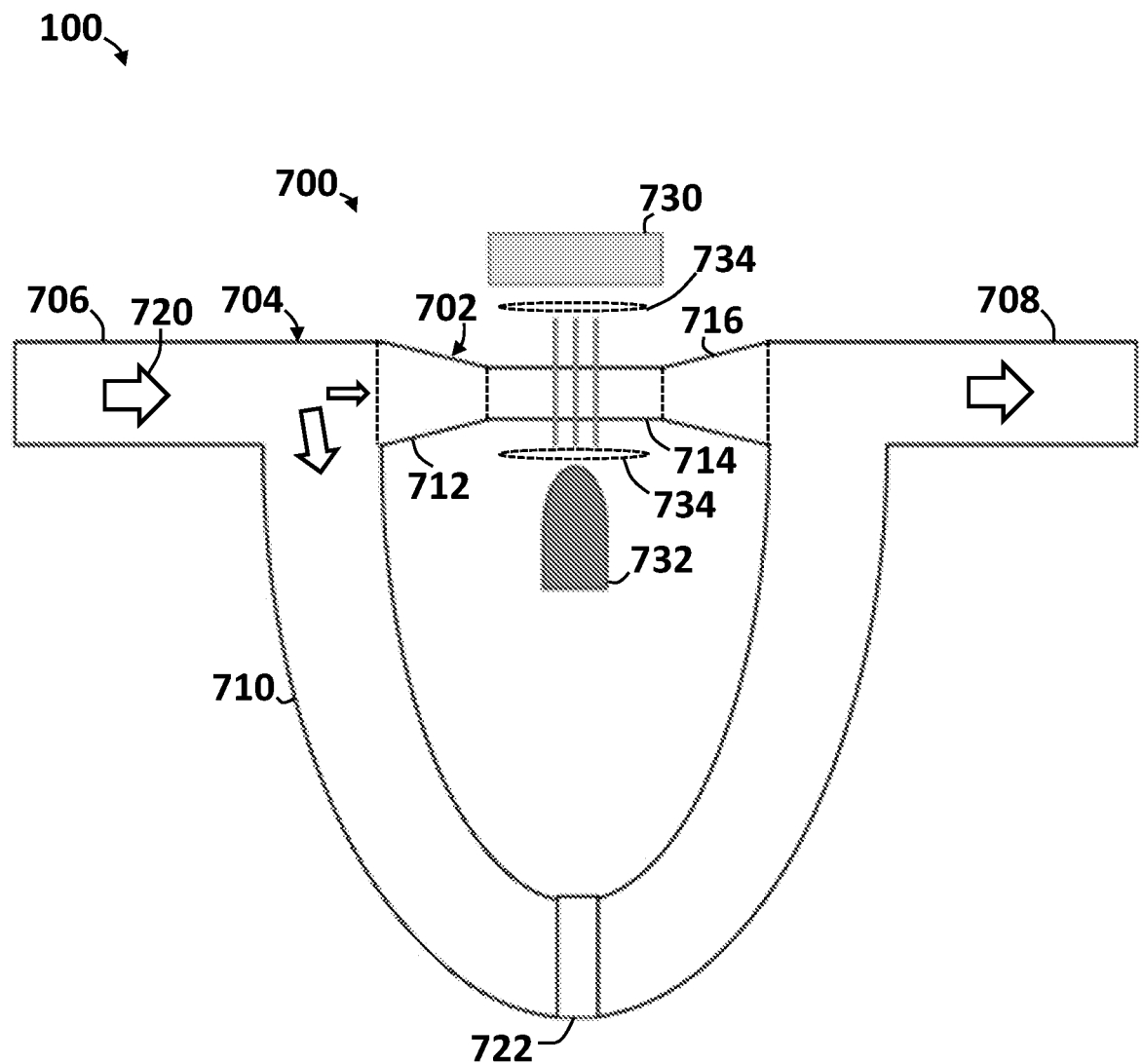
FIG. 10 illustrates a droplet sensor that may be used in the system of FIG. 1 having a converging-diverging nozzle.

FIG. 10 shows one example of a droplet sensor that may be used with system 100. Droplet sensor 700 includes microfluidic channel 702 positioned to receive a bypass flow from main flow channel 704. One or both of main flow channel 704 or microfluidic channel 702 may include a bend to separate the bypass flow from the main flow.

In the illustrated embodiment, microfluidic channel 702 forms a straight path with main flow inlet 706 and main flow outlet 708 of main flow channel 704. The straight geometry may prevent water drops or bubbles from being caught in microfluidic channel 702. The main flow follows a different path along main flow branch 710. As illustrated, main flow branch 710 is shown as a simple loop, but any suitable shape may be used to balance pressure and flow through the microchannel.

In some embodiments, microfluidic channel 702 may include a converging-diverging nozzle or converging-diverging nozzle design. The nozzle may improve pressure recovery, or otherwise control pressure losses, for example, by reducing the length of microfluidic channel 702. In the illustrated embodiment, the nozzle may be defined by inlet portion 712, sensing portion 714 (which may also be described as a throat of the nozzle), and outlet portion 716. In other embodiments, sensing portion 714 may be incorporated into the inlet portion 712 or the outlet portion 716.

In the illustrated embodiment, inlet portion 712 and outlet portion 716 each have widths that are variable, or that change, along their length. Length of microfluidic channel 702 is defined along an axis that extends along the direction of flow through microfluidic channel 702. Width of microfluidic channel 702 is generally orthogonal to length. Sensing portion 714 may have a width that does not change along its length, for example, when sensing portion 714 is not incorporated into inlet portion 712 or outlet portion 716.

Inlet portion 712 may taper in the direction of fluid flow, or flow direction, through microfluidic channel 702. The taper may be linear or non-linear (e.g., curved). Inlet portion 712 may define a contraction angle, which is a measurement that may represent the angle of a linear taper or may represent an average measurement representative of multiple measurements of angles in a non-linear taper. An angle may be measured from any suitable axis, such as an axis aligned to the direction of bypass fluid flow through microfluidic channel 702. Inlet portion 712 may be described as a contracting inlet portion.

Outlet portion 716 may flare in the direction of fluid flow, or flow direction, through microfluidic channel 702. The flare may be linear or non-linear (e.g., curved). Outlet portion 716 may define an expansion angle, which may be calculated in a similar manner to the contraction angle. An angle may be measured from any suitable axis, such as an axis aligned to the direction of bypass fluid flow. Outlet portion 716 may be described as an expanding outlet portion.

Inlet portion 712 and outlet portion 716 may also be described using a contraction ratio and an expansion ratio. As used herein, "contraction ratio" refers to the ratio of the cross-sectional area at the nozzle inlet (widest cross-sectional area of inlet portion 712 or at the widest opening of the inlet portion) and the throat (the smallest cross-sectional area, such as in the sensing portion 714). The "expansion ratio" refers to the ratio of the cross-sectional area at the nozzle outlet (widest cross-sectional area of outlet portion 716 or at the widest opening of the outlet portion). For example, a channel cross-sectional area that goes 300 micrometers down to 100 micrometers and back to 300 micrometers would have a contraction ratio of 3 and an expansion ratio of 3.

The lengths and corresponding angles of inlet portion 712 and outlet portion 716 may be the same or different. In some embodiments, the length of contracting inlet portion 712 is shorter than the length of the expanding outlet portion 716, or vice versa. In some embodiments, the contraction angle of inlet portion 712 may be greater than the expansion angle of outlet portion 716. In some embodiments, the expansion and contraction ratios may be the same or different. For example, the expansion ratio and the contraction ratio may be the same even though the corresponding lengths and angles are the different.

In the illustrated embodiment, main flow 720, or main fluid flow, enters from the left side of the illustration into microfluidic channel 702 from main flow inlet 706. The main flow 720 splits between main flow branch 710 and microfluidic channel 702. The bypass flow enters microfluidic channel 702 at inlet portion 712 and increases in fluid velocity, while flow rate remains the same, as the cross-section decreases in inlet portion 712 causing the static pressure head to decrease. After the bypass flow passes from inlet portion 712 and sensing portion 714 and enters outlet portion 716, the reverse occurs and the fluid velocity decreases, while flow rate remains the same, causing the static head pressure to increase. In other words, the fluid velocity may decrease, and the static head pressure may increase, after a minimum diameter of microfluidic channel 702 is encountered by the bypass flow. The bypass flow may then rejoin in the main flow after passing through outlet portion 716.

By controlling the contraction and expansion rates, the amount of pressure recovery may be controlled, for example, by minimizing flow separation within the system. In properly engineered devices, minimizing flow separation may lead to sustainably less pressure drop at a given channel length compared to a constant cross-sectional area channel length. The converging-diverging nozzle design of microfluidic channel 702 may be used to control the pressure drop through droplet sensor 700. A lower pressure drop may lead to additional flow through droplet sensor 700.

System 100 may include a flow restrictor to facilitate fluid flow through droplet sensor 700. In the illustrated embodiment, flow restrictor 722 may be positioned along the main flow channel 704, for example, in main flow branch 710. Flow restrictor 722 may facilitate driving more flow through microfluidic channel 702 compared to a system without flow restrictor 722. In some cases, without flow restrictor 722, less than or equal to 0.0001% of the main flow may enter microfluidic channel 702, for example, when a width or diameter of microfluidic channel 702 is 150 micrometers and a width or diameter of main flow channel 704 is 12 millimeters. In general, the relative width of microfluidic channel 702 is much smaller compared to main flow channel 704 than illustrated (e.g., at least one order of magnitude). In some embodiments, at least 0.1, 0.5, 1, 1.5, 2, 2.5, 5, or even 10% of the main flow may enter microfluidic channel 702, for example, when the converging-diverging nozzle or flow restrictor 722 is included.

Optical components may be used to increase the signal-to-noise ratio of droplet sensor 700, for example, by increasing the intensity of light from light source 730 directed at light detector 732. In one or more embodiments, droplet sensor 704 may include one or more optical components, such as focusing optics or a lens 734. One or more lenses 734 may be positioned generally between light source 730 and light detector 732. As illustrated one lens 734 is positioned between light source 730 and microfluidic channel 702, and another lens 734 is positioned between microfluidic channel 702 and light detector 732.

Figure 11:
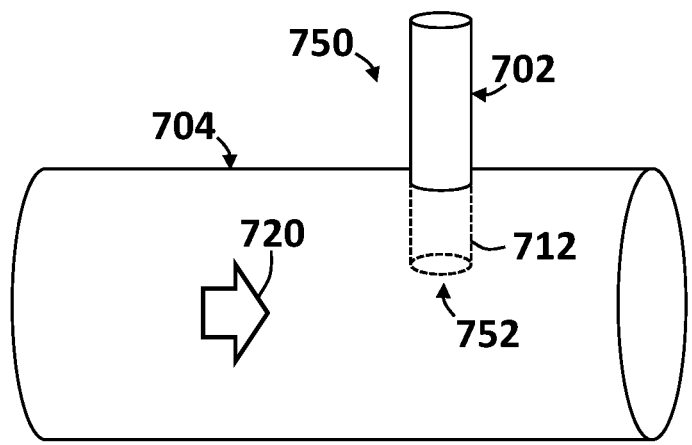
FIGS. 11-13 illustrate various droplet sensors that may be used in the system of FIG. 1 having a microfluidic channel extending into a main flow channel.
Figure 12:
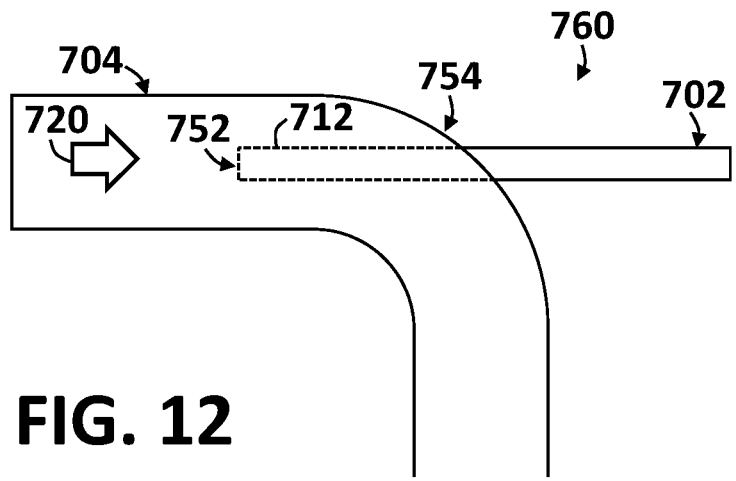
Figure 13:
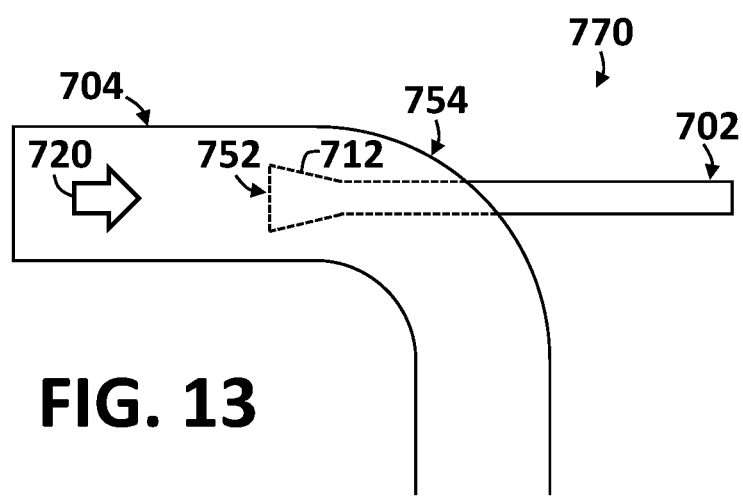

The microfluidic channel may be at least partially or fully submerged in the main flow of the fuel line. In some embodiments, an inlet of the microfluidic channel is positioned in the main flow or main flow channel. FIGS. 11-13 show various examples of positioning an inlet of the microfluidic channel to sample the main flow from the main flow channel. Main flow 720 through main flow channel 704 may be sampled by the droplet sensor from near the wall of main flow channel 704 (e.g., near the wall of the pipe) or from inside main flow channel 704 (e.g., inside the pipe). If main flow 720 is sampled from the middle of main flow channel 704, the main flow 720 may be sampled from a straight section of pipe or from a bend in the pipe. Inlet portion 712 of microfluidic channel 702 may include opening 752 positioned to capture a representative fluid sample for the droplet sensor, a sample in which the water drops are concentrated, or a sample in which water drops are diluted. In general, the center of main flow channel 704 may provide a representative fluid sample of main flow 720.

The opening 752 may have the same cross-sectional dimensions as microfluidic channel 702 or may be larger or smaller. Larger sensor inlet dimensions may be advantageous due to a lower pressure drop.

FIG. 11 shows droplet sensor 750, which includes opening 752 at a distal end of inlet portion 712 extending from a side of main flow channel 704 toward a center of main flow channel 704 to position opening 752 near the center of main flow channel 704. In the illustrated embodiment, main flow channel 704 extends linearly, or straight, and microfluidic channel 702 extends linearly, or straight, orthogonal to the direction of main flow 720.

Main flow channel 704 may extend linearly or non-linearly. In some embodiments, one or more droplet sensor embodiments may also be used with a main flow channel having a bend or other non-linear geometry. FIG. 12 shows droplet sensor 760, which includes opening 752 at a distal end of inlet portion 712 extending from bend 754 in main flow channel 704 to a center of main flow channel 704 to position opening 752 near the center of main flow channel 704. In the illustrated embodiment, main flow channel 704 is non-linear. Microfluidic channel 702 enters into main flow channel 704 at bend 754.

Inlet portion 712 of microfluidic channel 702 may be straight or include a taper (or converging nozzle). FIG. 13 shows droplet sensor 770, which includes opening 752 at a distal end of inlet portion 712 extending from bend 754 to a center of main flow channel 704 to position opening 752 near the center of main flow channel 704. Inlet portion 712 is at least partially tapered and opening 752 is larger compared to droplet sensor 760 (FIG. 12). In the illustrated embodiment, main flow channel 704 extends linearly, or straight, and microfluidic channel 702 extends linearly, or straight, along the direction of main flow 720.

The microfluidic channel may be entirely submerged in the main flow channel. In particular, the inlet and the outlet of the microfluidic channel may be positioned in the main flow of the main flow channel. In some embodiments, the droplet sensor may be in an annular flow configuration, in which the microfluidic sensor channel is contained within the main flow channel. The microfluidic channel may be located at the center of the main flow channel or away from the center.

The microfluidic sensor channel may be oriented in any suitable manner within the main flow channel. In some embodiments, the microfluidic sensor channel may run parallel to the direction of fluid flow or at an angle. The light source and detector may be submersed in the main flow channel, encapsulated and submersed, or coupled to the microfluidic channel with fiber optics, light guides, waveguides, or the like. The microfluidic channel may have a constant cross-sectional dimension (e.g., width) or may vary along its length. Varying the microfluidic sensor channel dimensions may be advantageous by lowering pressure drop or increasing sampling volume.

FIGS. 14A-B and 15A-B show various examples of microfluidic channels submerged in a main flow channel, which may facilitate having fewer bends in the path of fluid flow. FIGS. 14A-B show one example of a droplet sensor with the light source and light detector submerged in a main flow channel. Droplet sensor 800 includes light source 802, light detector 804, and microfluidic channel 806. In particular, inlet 807 (e.g., opening or inlet portion) and outlet 809 (e.g., opening or outlet portion) of microfluidic channel 806 are submerged in main flow channel 810. Microfluidic channel 806 may be described as being surrounded by a wall, or interior surface, of main flow channel 810.

To hold a substrate forming microfluidic channel 806 in the main flow, one or more supports 812, or support structures, may be coupled to main flow channel 810. In the illustrated embodiment, one support 812 is coupled between light source 802 and a wall of main flow channel 810. Another support 812 is coupled between light detector 804 and a wall of main flow channel 810 and may be on the opposite side of main flow channel 810 or microfluidic channel 806 than the other support. The substrate forming microfluidic channel 806 may be coupled to light source 802 or a first support 812 and may be coupled to light detector 804 or a second support 812 to be held, for example, near a center of the main flow. Supports 812 may be made of any suitable material to mechanically couple different components of the droplet sensor 800.

Microfluidic channel 806 may be formed from a substrate or defined between two or more optical components, for example, instead of being formed only from a substrate. In some embodiments, microfluidic channel 806 may be defined between two or more optical components, such as a light source, light detector, light aperture, light channel, lens, and separate microfluidic channel substrate. In some embodiments, microfluidic channel 806 may be formed of a glass tube as the substrate.

One example of a light channel is a fiber optic channel, or a channel formed by fiber optics. Use of fiber optics may allow certain optical components of the droplet sensor to be positioned outside of the main flow channel. FIGS. 15A-B show one example of a droplet sensor with fiber optics at least partially submerged in a main flow channel that form a microfluidic channel. Droplet sensor 820 includes light source 802, light detector 804, and fiber optics 814. In the illustrated embodiment, light source 802 and light detector 804 are positioned outside of main flow channel 810 and optically coupled to the interior of main flow channel 810 through fiber optics 814. The microfluidic channel 826 may be defined in length and width by end portions of optical fibers of fiber optics 814, for example, instead of a separate microfluidic channel substrate.

Various combinations of optical components may also be used to form the microfluidic channel. In some embodiments, a light source and a fiber optic channel may be used to define the microfluidic channel. In other embodiments, a light detector and a fiber optic channel may be used to define the microfluidic channel. In still further embodiments, the light source and light detector may be contained within main flow channel and define the microfluidic channel.

Optical components forming the microfluidic channel may be described as forming a virtual microfluidic channel between the two components. That is, the path length between the two components creates the microfluidic channel. The light detector or light source may be coupled to, or positioned relative to, a light aperture to define the virtual microfluidic channel.

In general, one or both of the light source and detector may be outside the main flow channel, where fiber optics, light guides, waveguides, or the like may be used to bring the light into or out of the main flow channel to or from the virtual microfluidic channel. Utilizing the virtual microfluidic channel may reduce pressure drop relative to using a separate substrate only to form the microfluidic channel.

Sensors similar to the droplet sensors described herein may also be used to detect water without a microfluidic channel. In some embodiments, such a sensor may be used to detect when a water volume or water level (e.g., based on height) has reached a certain threshold or used to monitor water level continuously. In some trucking applications, for example, understanding water height may help a truck operator understand when to drain water from the fuel system because a certain water volume has been collected. Existing water sensors in trucking applications utilize a mechanical float, which may be prone to fouling, or a resistive or conductive probe, which may also be prone to fouling through electroplating or deposits.

Figure 16:
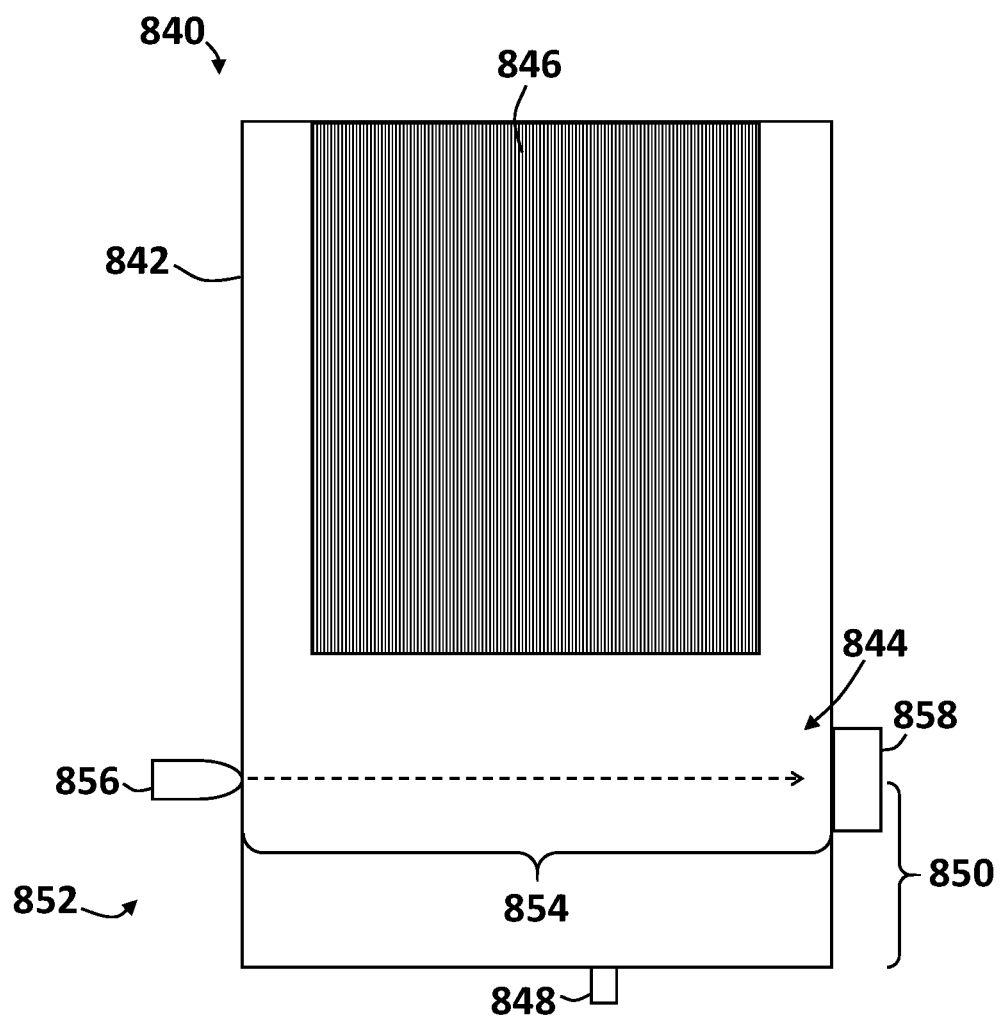
FIGS. 16-18 illustrate various fuel water separators, or fuel filters, that may be used in the system of FIG. 1 including a water level sensor.
Figure 17:
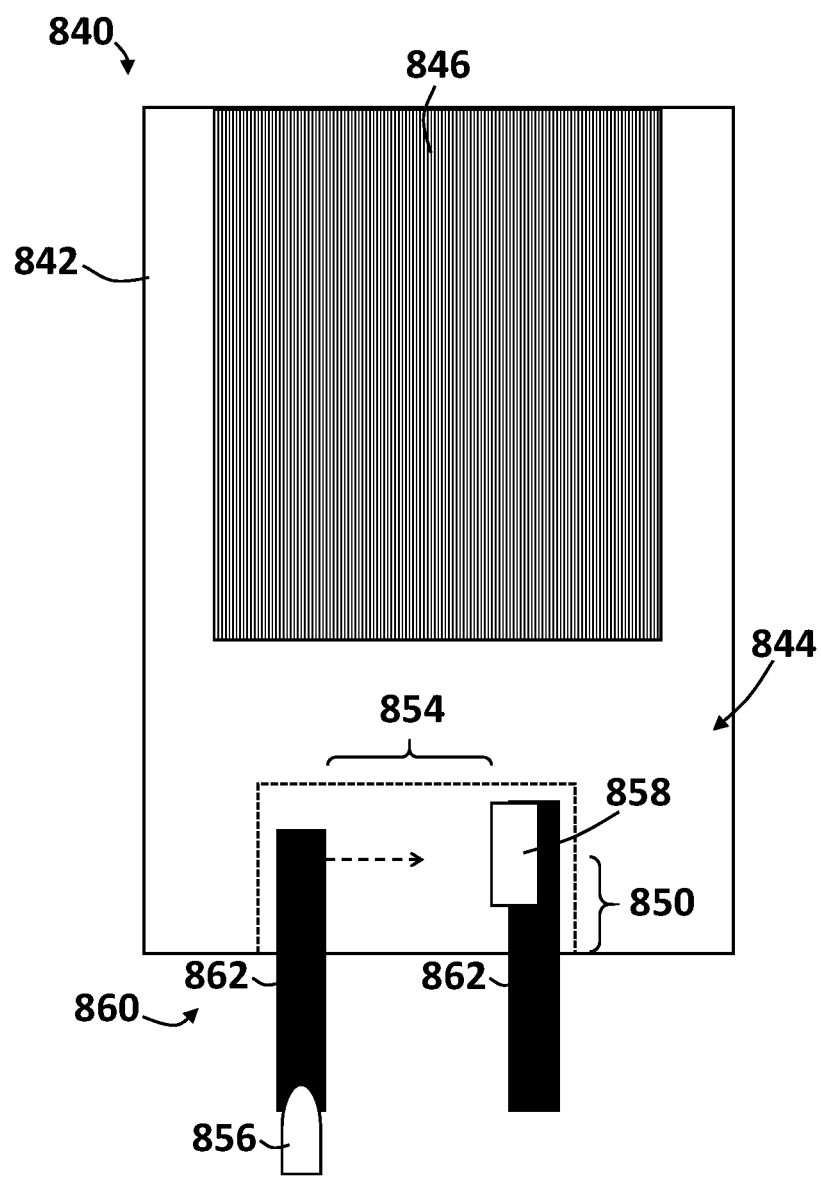
Figure 18:
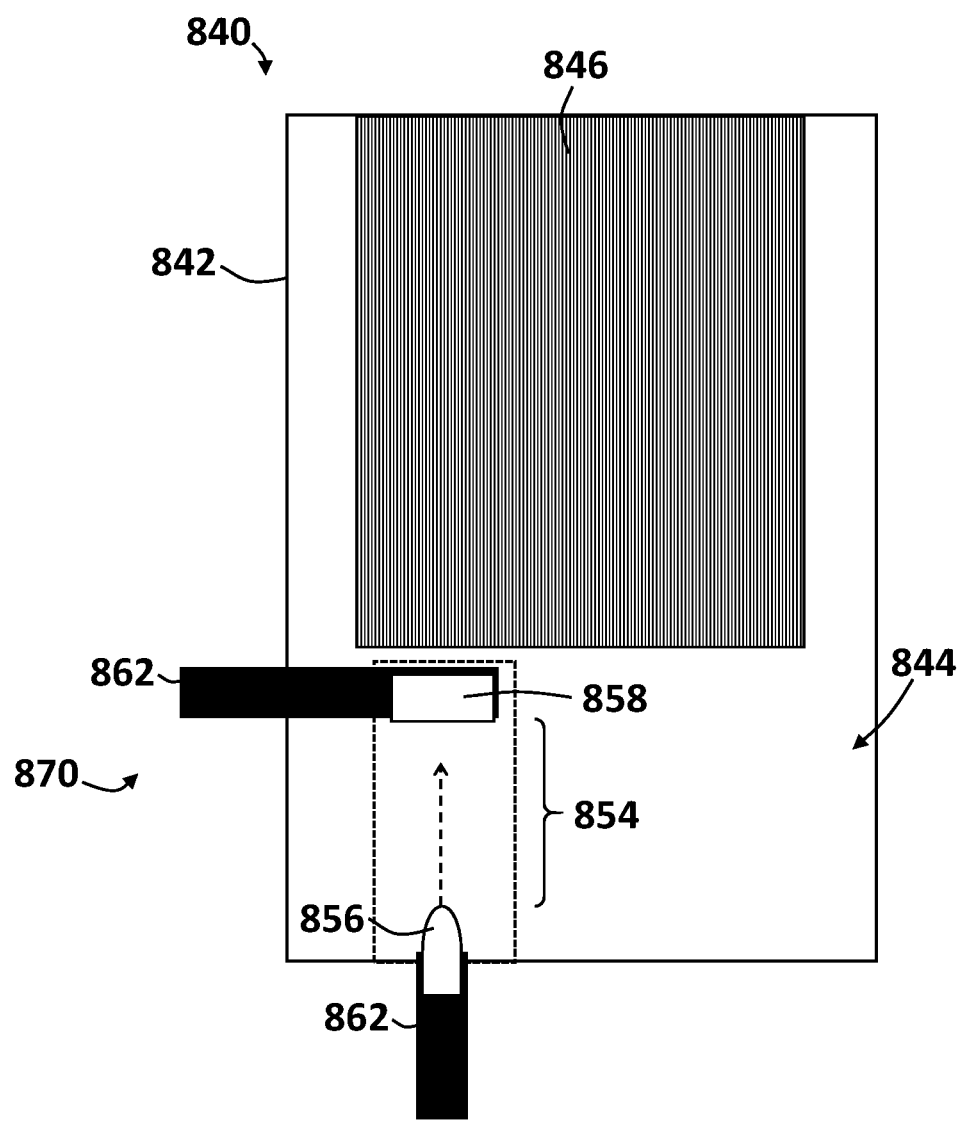

FIGS. 16-18 show various embodiments of sensors, such as water level sensors, used without a microfluidic channel in a fuel water separator or fuel filter, such as fuel filter 116 (FIG. 1). When water is removed from a fuel system using a filter, the water may be collected in the bottom of a housing 842 of fuel water separator 840 in a water collection volume 844, or bowl, after fuel is filtered. The water collection volume 844 may be fluidly connected to an engine fuel line (e.g., main flow channel) fluidly connected to filter element 846 and water drain outlet 848 to selectively drain water when water has reached threshold water level 850. In general, the water collection volume 844 may be upstream of filter element 846 or downstream of filter element 846.

Sensor 852 may be positioned at a height of water collection volume 844 corresponding to detect water reaching threshold water level 850. Sensor 852 may include light source 856, which may be a near-infrared light source. Sensor 852 may also include light detector 858, which may be a photodetector. Light source 856 and light detector 858 may be positioned to define threshold water level 850 in the water collection volume 844. The distance or space between lights source 856 and light detector 858 may define path length 854.

A controller (which may be similar to controller 106 of FIG. 8) may be operably coupled to light detector 858 and optionally light source 856. The controller may be configured to determine that water in water collection volume 844 has reached threshold water level 850 in response to the signal from light detector 858. In general, when water is present between light source 856 and light detector 858 along path length 854, in response, the controller may determine that the water volume has reached threshold water level 850.

Various configurations of sensor 852 may be used to measure the water level. FIG. 16 shows sensor 852 having light source 856 and light detector 858 positioned outside of water collection volume 844 and housing 842. In other embodiments, one or both of light source 856 and light detector 858 may be positioned inside water collection volume 844 or housing 842 and may be submersible in water.

FIG. 17 shows another example of a sensor configuration. Sensor 860 is similar to sensor 852 and further includes optical components 862, or fiber optics. Optical components 862 may be used to couple light from light source 856 or light detector 858 into or out of water collection volume 844. In the illustrated embodiment, light source 856 is positioned outside water collection volume 844 and is optically coupled to optical component 862 to direct a light beam into water collection volume 844 and toward light detector 858. Light detector 858 is positioned inside water collection volume 844 to receive the light beam and is optically coupled to another optical component 862 to direct the light beam outside of water collection volume 844. Path length 854 may be defined between optical component 862 coupled to light source 856 and light detector 858.

FIG. 18 shows yet another example of a sensor configuration. Sensor 870 is similar to sensor 860 and is oriented to measure a water level by defining path length 854 in a direction to measure rising water levels (e.g., vertically). In particular, light source 856 and light detector 858 are positioned to measure a water level in water collection volume 844 and the controller (which may be similar to controller 106 of FIG. 8) is configured to determine the water level in response to the signal. As the water level rises along path length 854, the absorptivity detected by light detector 858 will increase, and the controller may determine the water level, for example, in proportion to the increase in absorptivity. In the illustrated embodiment, light source 856 and light detector 858 are positioned inside water collection volume 844 and housing 842. In other embodiments, light source 856 and light detector 858 may be positioned outside water collection volume 844 or housing 842.

In general, a near-infrared light source and detector may be placed outside the water collection bowl. If the near-infrared light source and detector are outside the water collection volume, they may be coupled with fiber optics, wave guides, light guides (or similar) to bring the incoming light into the bowl, and to collect the transmitted light and bring it back out of the bowl. In some embodiments, one of the light source and detector may be in the water collection volume, while the other component may be outside the water collection bowl connected by a fiber optic, wave guide, or light guide. In other embodiments, both the light source and detector may be in the water collection volume.

The path length of the light may consist of a portion of the water collection volume width or height or may include the entire water collection bowl width or height. If the path length of light is the entire water collection volume width or height, the housing of the fuel water separator may be made from a material transparent to near-infrared light (e.g., glass) such that the light source and detector are outside the housing. If the sensor is oriented with the water collection bowl width, the sensor can act as a trigger once the water has reached the height of the sensor. If the sensor is oriented with the water collection bowl height (or at an oblique angle), the sensor can act as a continuous water level sensor as a decrease in transmitted light may indicate an increase in water height.

Figure 19:
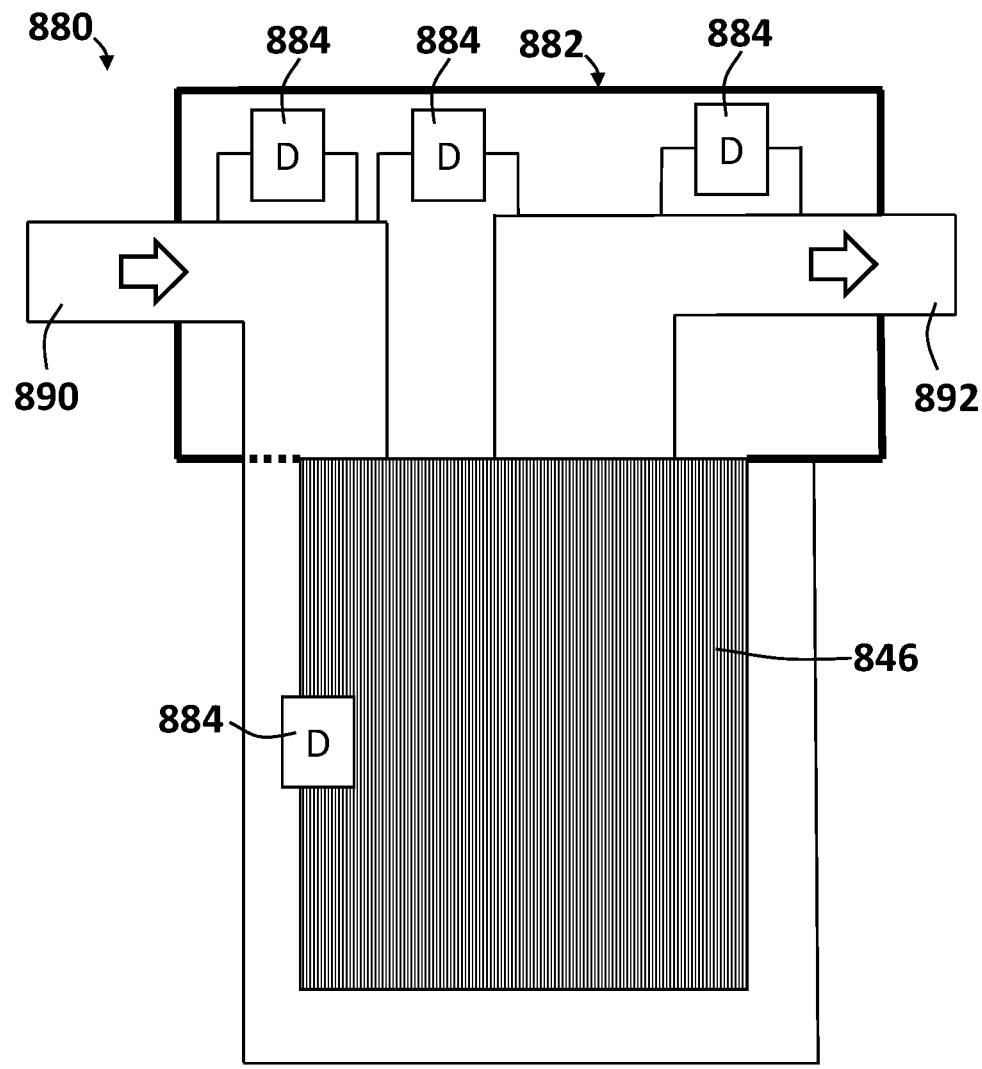
FIG. 19 illustrates various positions for sensors in a fuel water separator that may be used in the system of FIG. 1.

FIG. 19 shows one example of a fuel water separator including a filter head. In the illustrated embodiment, various positions for a sensor or droplet sensor 884 are shown within fuel water separator 880. In some embodiments, one or more droplet sensors 884 may be positioned in filter head 882. Filter head 882 may include an inlet and an outlet in fluid communication with a main flow channel and the filter element. Droplet sensor 884 may be positioned to sample along inlet 890, along outlet 892, between inlet and outlet, or even along or within filter element 846.

In general, a microfluidic water sensor, or droplet sensor, may be integrated directly into the filter head. The sensor could be placed in the inlet or outlet of the filter head. The sensor could be a bypass to the filter connecting the inlet and outlet directly. The sensor may be incorporated directly into a replaceable filter element.

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

Examples

Figure 20:
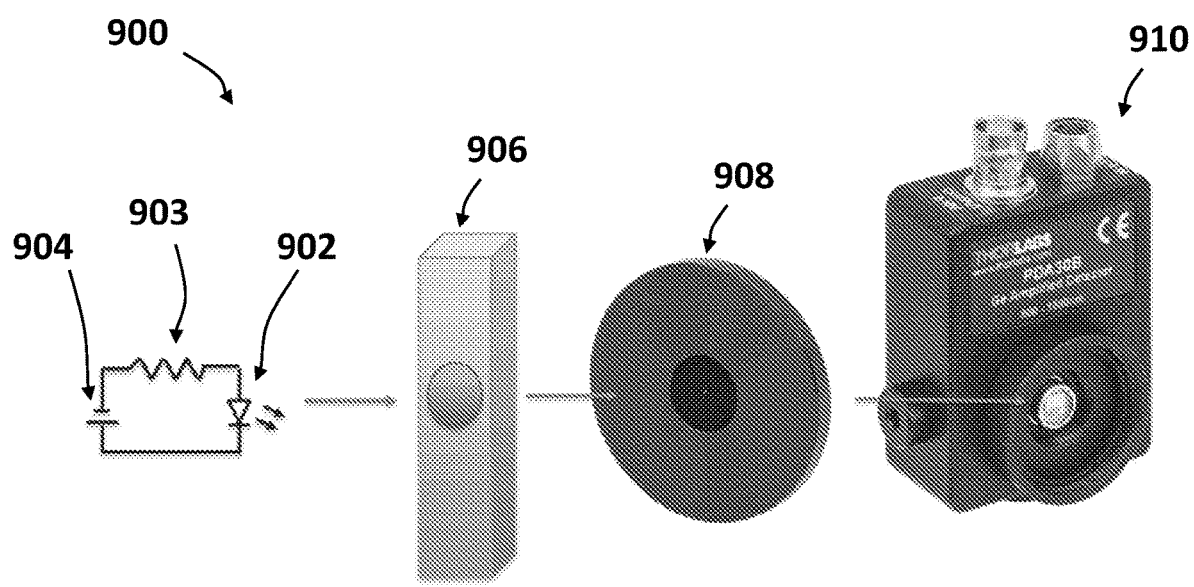
FIG. 20 illustrates an experimental setup including a detection assembly.

In Example 1, detection assembly 900 was provided as shown in FIG. 20. Detection assembly 900 included a near-infrared light-emitting diode (LED) 902, which was centered at 1550 nm (available from Thorlabs, Newton, N.J.). LED 902 was driven by commercially-available 5V power source 904 connected using a Universal Seral Bus (USB) port. LED 902 was connected in series with a commercially available 51Ω resistor 903. Light from LED 902 was not focused by an optics. LED 902 was brought into close proximity to microfluidic device 906, made of poly (dimethylsiloxane) (PDMS) (available under trade name DOW CORNING SYLGARD 184) and glass, which defined a microfluidic channel. Microfluidic device 906 included a T-Junction droplet generator that fed water drops into the microchannel of microfluidic device 906. The microchannel, or microfluidic channel, had a width of 150 micrometers and a depth of 140 micrometers. The channel was aligned with 150 μm-pinhole light aperture 908 (available from Thorlabs). Light from LED 902 was directed through the light aperture 908 and the microfluidic channel of microfluidic device 906 to be detected by a PDA30B germanium (Ge) transimpedance amplified light detector 910 (available from Thorlabs, Newton, N.J.). The output signal was transferred via a 50Ω BNC cable to a TDS 2014C oscilloscope (available from Tektronix, Beaverton, Oreg.).

Figure 21:
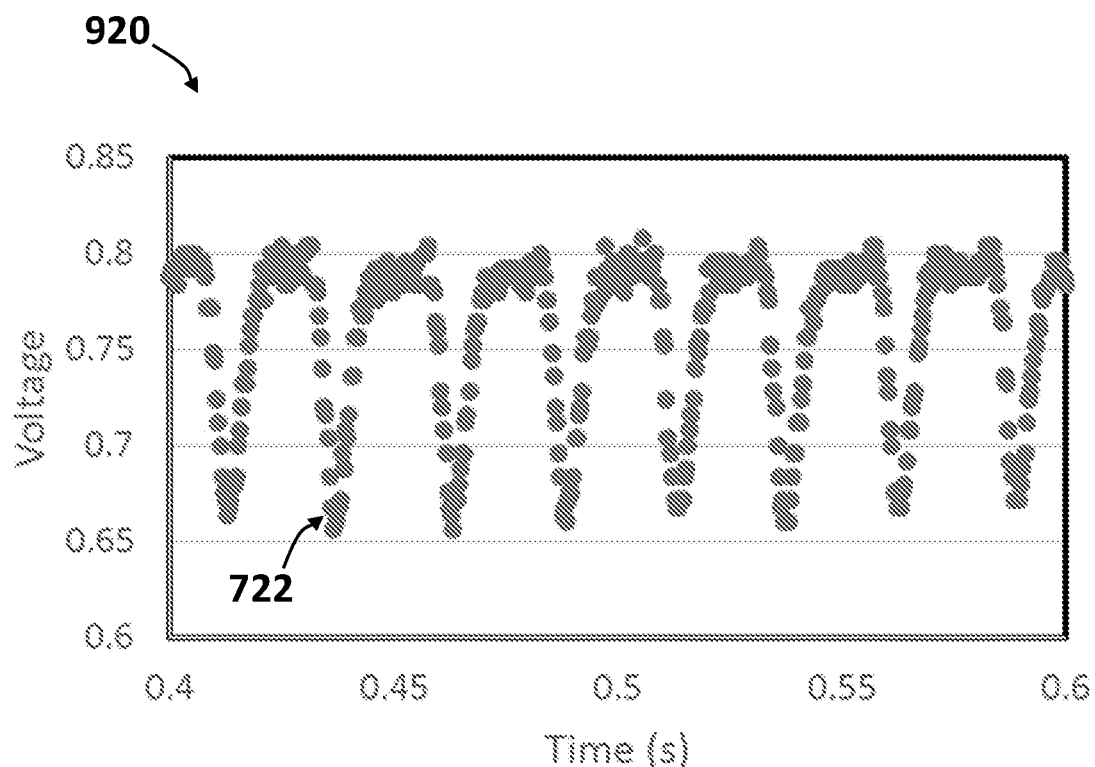
FIG. 21 illustrates a light detector signal plot using the detection assembly of FIG. 20.

A flow of fuel at 25 microliters per minute and a flow of water at 2 microliters per minute were provided to detection assembly 900 using syringe pumps (available from Harvard Apparatus, Holliston, Mass.), which resulted in the formation of water droplets. As determined from signal analysis, the water droplets had a diameter of 117 micrometers at a droplet rate of 40 droplets per second. Measurements were taken using the TDS 2014C oscilloscope set at a probe attenuation of 10×. FIG. 21 shows plot 920 of voltage (V) versus time (s) of signal 922 from the TDS 2014C oscilloscope. Each dip in signal 922 corresponded to a droplet moving through a sensing area defined by detection assembly 900.

Figure 22:
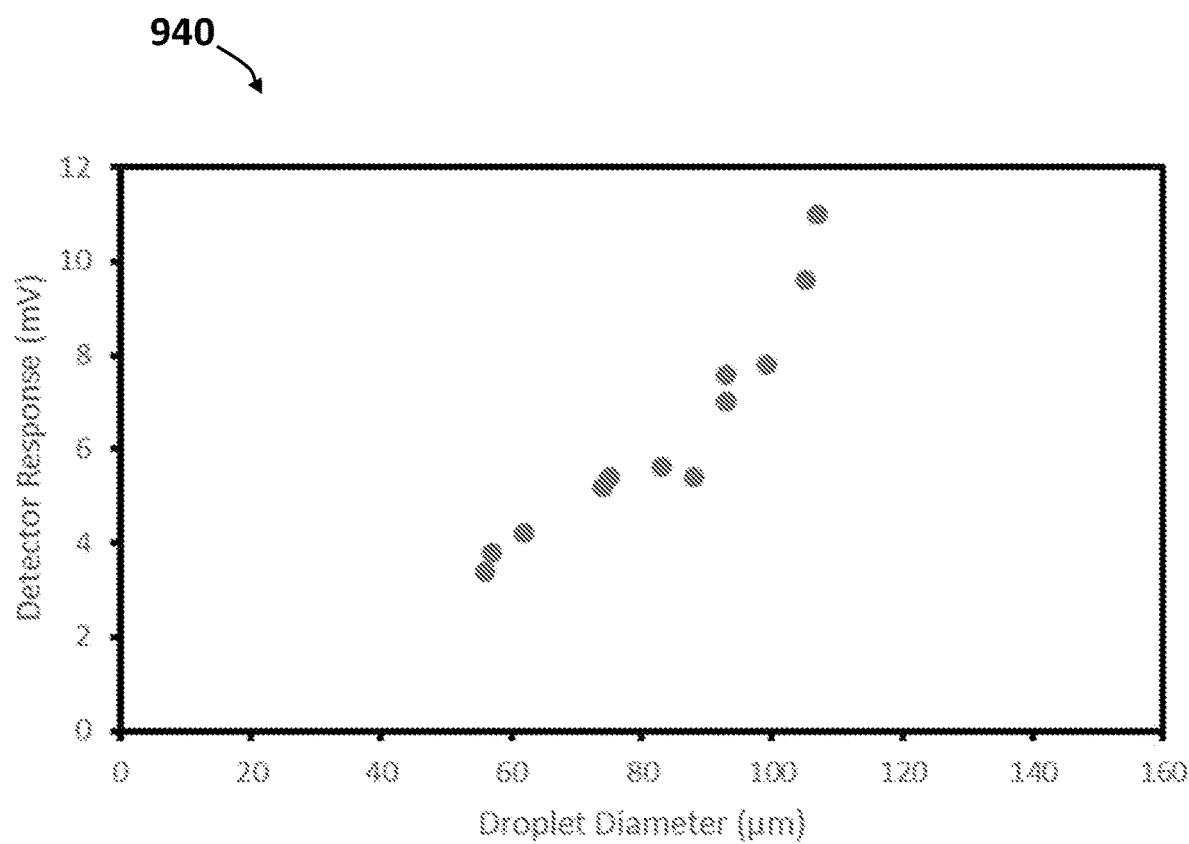
FIG. 22 illustrated a light detector signal plot using a detection assembly with a flow focusing droplet generator.

In Example 2, a detection assembly was fed with drops smaller than the dimensions of the microchannel of a microfluidic device to test whether the detector response would correspond, or correlate, to droplet diameter. The detection assembly was the same as detection assembly 900, except that the microfluidic device used a flow focusing droplet generator was used instead of a T-Junction droplet generator was used to feed the microchannel and the oscilloscope was set at a 1× attenuation. From signal analysis, droplet frequency and size were determined. As illustrated in FIG. 22, plot 940 shows the output voltage drop of the detector in millivolts (mV) for various droplet sizes (µm or micrometers). As can be seen, the greater voltage drops correspond to greater droplet diameters when the droplet is smaller than the width of the microchannel.

Illustrative Embodiments

In embodiment A1, a system comprises a microfluidic channel configured to receive a flow of a first fluid and a second fluid dispersed in the first fluid. The second fluid has a different composition than the first fluid. The system also comprises a light source configured to direct a light beam in a frequency band along a path through the microfluidic channel. The frequency band is selected to have a higher absorbance by the second fluid than by the first fluid. The system further comprises an aperture element defining a light aperture positioned in the path of the light beam from the light source. The system further comprises a light detector positioned to receive the light beam in a sensing area after passing through the microfluidic channel and the light aperture. The light detector is configured to provide a signal representing an amount of light in the frequency band that remains after passing through the microfluidic channel. The system further comprises a controller operably coupled to the light detector and configured to determine whether the second fluid is in droplet form based on the signal.

In embodiment A2, a system comprises the system according to any A embodiment, wherein the controller is further configured to determine an amount of second liquid in droplet form per unit volume of first fluid based on the signal. The amount optionally excludes second fluid dissolved in first fluid.

In embodiment A3, a system comprises the system according to any A embodiment, further comprising a controller operably connected to the light detector and configured to detect a droplet rate or a droplet size of one or more droplets of the second fluid dispersed in the flow of the first fluid based on the signal.

In embodiment A4, a system comprises the system according to embodiment A3, wherein the controller is further configured to determine the droplet rate or the droplet size based on at least one of: a magnitude of a pulse contained within the signal, a width of a pulse contained within the signal, a first threshold signal level for detecting a minimum size droplet in the sensing area, a second threshold signal level for detecting a droplet that fills the sensing area, and a threshold signal level crossing rate.

In embodiment A5, a system comprises the system according to embodiment A4, wherein the controller is further configured to determine at least one of: an amount of second liquid in droplet form per unit volume of first fluid based on the droplet rate and droplet size; the droplet size based on the magnitude of a pulse contained within the signal in response to the signal not crossing the second threshold signal level; the droplet size based on the width of a pulse contained within the signal in response to the signal crossing the second threshold signal level; and the droplet size based on the droplet rate.

In embodiment A6, a system comprises the system according to any A embodiment, wherein the microfluidic channel is at least one of: in parallel fluid communication with a main flow of a fuel line; at least partially submerged in the main flow of the fuel line, wherein an inlet of the microfluidic channel is positioned in the main flow of the fuel line or the inlet and an outlet of the microfluidic channel is positioned in the main flow of the fuel line; and defined between two or more optical components selected from: the light source, the light detector, the light aperture, a light channel, a lens, and a separate microfluidic channel substrate.

In embodiment A7, a system comprises the system according to any A embodiment, wherein the microfluidic channel comprises a converging-diverging nozzle.

In embodiment A8, a system comprises the system according to embodiment 7, wherein: the converging-diverging nozzle of the microfluidic channel comprises a contracting inlet portion and an expanding outlet portion along a flow direction; and optionally wherein a length of the contracting inlet portion is shorter than a length of the expanding outlet portion.

In embodiment A9, a system comprises the system according to any A embodiment, wherein the controller is further configured to detect a droplet of the second liquid of a predetermined size having an equivalent volume to a droplet of the second liquid having a spherical diameter in a range from 10 up to 1000 micrometers.

In embodiment A10, a system comprises the system according to any A embodiment, wherein the first fluid comprises a hydrocarbon fluid and the second fluid comprises water.

In embodiment A11, a system comprises the system according to any A embodiment, further comprising at least one of: a fuel line configured to deliver fuel a fuel injector; a fuel filter configured to filter water from gasoline or diesel fuel positioned along the fuel line; and a fuel pump in fluid communication with the fuel line, wherein the fuel pump is configured to provide fuel flow to the fuel injector along the fuel line.

In embodiment A12, a system comprises the system according to any A embodiment, further comprising another microfluidic channel positioned between the light source and the light detector.

In embodiment A13, a system comprises the system according to any A embodiment, wherein the microfluidic channel defines a cross-sectional area less than 1 mm$^2$ and the light aperture has a width less than 1 mm to define the sensing area.

In embodiment A14, a system comprises a fuel and water separator comprising a housing defining a water collection volume. The water collection volume is fluidly connected to an engine fuel line and fluidly connected to a water drain outlet. The system also comprises a light source configured to direct a light beam in a frequency band along a path through the water collection volume. The frequency band is selected to be absorbed by water. The system further comprises a light detector positioned to receive the light beam in a sensing area after passing through at least part of the water collection volume. The light detector is configured to provide a signal representing an amount of light in the frequency band. The system further comprises a controller operably coupled to the light detector and configured to determine whether water is detected based on the signal.

In embodiment A15, a system comprises the system according to embodiment A14, wherein: the light source and light detector are positioned to define a threshold water level in the water collection volume and the controller is configured to determine that water in the water collection volume has reached the threshold water level in response to the signal; or the light source and the light detector are positioned to measure a water level in the water collection volume and the controller is configured to determine the water level in response to the signal.

In embodiment B1, a system comprises a microfluidic channel configured to receive a flow of hydrocarbon fluid. The microfluidic channel has a cross-sectional area sized to receive one water droplet at a time when a water droplet of a predetermined size is dispersed in the hydrocarbon fluid. The system also comprises a light source positioned outside the microfluidic channel configured to generate light in a selected frequency band such that the water droplet has a higher absorbance than the hydrocarbon fluid in the selected frequency band. The system further comprises a light detector sensitive to the selected frequency band positioned outside the microfluidic channel and configured to provide a signal representing an amount of light remaining after passing through the microfluidic channel. The system further comprises a light aperture positioned between the light source and the light detector. Light from the light source passing through the light aperture forms a light beam defining a beam axis that extends through the light source, the microfluidic channel, and the light detector. The system further comprises a controller operably connected to the light detector and configured to detect one or more water droplets dispersed in the flow of hydrocarbon fluid based on the signal from the light detector representing the amount of light from the light source remaining after passing through the microfluidic channel and the light aperture.

In embodiment B2, a system comprises the system according to any B embodiment, wherein the controller is configured to determine an amount of water per unit volume excluding dissolved water based on the signal from the light detector.

In embodiment B3, a system comprises the system according to any B embodiment, wherein the controller is configured to detect the water droplet of the predetermined size having a volume corresponding to a spherical diameter in a range from 10 up to 1000 micrometers based on the signal from the light detector.

In embodiment B4, a system comprises the system according to any B embodiment, wherein the controller is configured to provide a maintenance signal in response to detecting water in hydrocarbon fluid based on the signal from the light detector.

In embodiment B5, a system comprises the system according to any B embodiment, further comprising a fuel line configured to deliver fuel as the hydrocarbon fluid to a fuel injector, wherein the microfluidic channel is in parallel fluid communication with the fuel line.

In embodiment B6, a system comprises the system according to embodiment B5, further comprising a fuel filter configured to filter water from gasoline or diesel fuel positioned along the fuel line.

In embodiment B7, a system comprises the system according to embodiment B6, further comprising a fuel pump in fluid communication with the fuel line, wherein the fuel pump is configured to provide fuel flow to the fuel injector along the fuel line.

In embodiment B8, a system comprises the system according to any B embodiment, further comprising another microfluidic channel positioned between the light source and the light detector. The controller is further configured to detect one or more water droplets dispersed in a flow of hydrocarbon fluid through the another microfluidic channel based on the signal from the light detector.

In embodiment C1, a sensor comprises a microfluidic channel sized to receive a flow of fluid. The microfluidic channel has a cross-sectional area sized to receive one liquid droplet at a time when a liquid droplet of a different liquid of a predetermined size is dispersed in the fluid. The sensor also comprises a light source positioned outside the microfluidic channel configured to generate light in a selected frequency band such that the droplets have a different absorbance than the different liquid in the selected frequency band. The sensor further comprises a light detector sensitive to the selected frequency band positioned outside the microfluidic channel and configured to provide a signal representing an amount of light remaining after passing through the microfluidic channel. The sensor further comprises a light aperture positioned between the light source and the light detector. Light from the light source passing through the light aperture forms a light beam defining a beam axis that extends through the light source, the microfluidic channel, and the light detector. A width of the light aperture and the light detector define a sensing area. The sensor further comprises a controller operably connected to the light detector and configured to determine a droplet rate through the sensing area of the microfluidic channel based on the signal from the light detector representing the amount of light from the light source remaining after passing through the microfluidic channel and the light aperture.

In embodiment C2, a sensor comprises the sensor according to any C embodiment, wherein the controller is configured to determine the droplet rate or a droplet size based on at least one of: a magnitude of a pulse contained within the signal, a width of a pulse contained within the signal, a first threshold signal level for detecting a minimum size droplet in the sensing area, a second threshold signal level for detecting a droplet that fills the sensing area, and a threshold signal level crossing rate.

In embodiment C3, a sensor comprises the sensor according to any C embodiment, wherein the controller is configured to determine an amount of droplet liquid per unit volume based on the droplet rate and droplet size.

In embodiment C4, a sensor comprises the sensor according to any C embodiment, wherein the controller is configured to determine the droplet size based on the magnitude of a pulse contained within the signal when the signal level does not cross the second threshold signal level.

In embodiment C5, a sensor comprises the sensor according to any C embodiment, wherein the controller is configured to determine the droplet size based on the width of a pulse contained within the signal when the signal level crosses the second threshold signal level.

In embodiment C6, a sensor comprises the sensor according to any C embodiment, wherein the controller is configured to determine a droplet size based on the droplet rate.

In embodiment D1, a water droplet sensor comprises a microfluidic channel defining a cross-sectional area less than 1 mm$^2$, a light source positioned outside the microfluidic channel configured to generate light in a near infrared frequency band, a light detector sensitive to the frequency band positioned outside the microfluidic channel and configured to provide a signal representing an amount of light remaining after passing through the microfluidic channel, and a light aperture positioned between the light source and the light detector. Light from the light source passing through the light aperture forms a light beam defining a beam axis that extends through the light source, the microfluidic channel, and the light detector. The aperture has a width less than 1 mm. The sensor also comprises a controller operably connected to the light detector and configured to detect one or more water droplets dispersed in a flow of hydrocarbon fluid based on the signal from the light detector representing the amount of light from the light source remaining after passing through the microfluidic channel and the light aperture.

In embodiment D2, a sensor comprises the sensor according to any D embodiment, wherein the light source is configured to generate light centered in the range from 1400 to 1600 nanometers.

In embodiment D3, a sensor comprises the sensor according to any D embodiment, wherein a path length of the light beam from the light aperture to the light detector is less than or equal to 1000 micrometers.

In embodiment D4, a sensor comprises the sensor according to any D embodiment, wherein at least one of a channel width of the microfluidic channel and the width of the aperture is less than or equal to 500 micrometers.

In embodiment D5, a sensor comprises the sensor according to any D embodiment, wherein a channel depth of the microfluidic channel is less than or equal to a channel width of the microfluidic channel.

In embodiment D6, a sensor comprises the sensor according to any D embodiment, wherein the width of the aperture is less than or equal to a channel width of the microfluidic channel.

Thus, various embodiments of the DROPLET SENSORS FOR FUEL SYSTEMS are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "less than or equal to" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, sensor controller may be operatively connected to vehicle computer to send and receive data).

Terms related to orientation, such as "top," "bottom," "upstream," and "downstream," are used to describe relative positions of components and are not meant to limit the orientation of the embodiments contemplated.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like.

The phrases "at least one of," "comprises at least one of," and "one or more of" followed by a list refers to any one of the items in the list and any combination of two or more items in the list.

What is claimed is:

1. A system comprising:
   a microfluidic channel configured to receive a flow of a first fluid and a second fluid dispersed in the first fluid, wherein the second fluid has a different composition than the first fluid;
   a light source configured to direct a light beam in a frequency band along a path through the microfluidic channel, wherein the frequency band is selected to have a higher absorbance by the second fluid than by the first fluid;
   an aperture element defining a light aperture positioned in the path of the light beam from the light source;
   a light detector positioned to receive the light beam in a sensing area after passing through the microfluidic channel and the light aperture, the light detector configured to provide a signal representing an amount of light in the frequency band that remains after passing through the microfluidic channel; and
   a controller operably coupled to the light detector and configured to determine whether the second fluid is in droplet form based on the signal, wherein the microfluidic channel is in parallel fluid communication with a main flow of a vehicle engine fuel line.

2. The system according to claim 1, wherein the controller is further configured to determine an amount of second liquid in droplet form per unit volume of first fluid based on the signal, wherein the amount of second liquid in droplet form excludes second fluid dissolved in first fluid.

3. The system according to claim 1, wherein the controller is configured to detect a droplet rate or a droplet size of one or more droplets of the second fluid dispersed in the flow of the first fluid based on the signal.

4. The system according to claim 3, wherein the controller is further configured to determine the droplet rate or the droplet size based on at least one of: a magnitude of a pulse contained within the signal, a width of a pulse contained within the signal, a first threshold signal level for detecting a minimum size droplet in the sensing area, a second threshold signal level for detecting a droplet that fills the sensing area, and a threshold signal level crossing rate.

5. The system according to claim 4, wherein the controller is further configured to determine at least one of:
an amount of second liquid in droplet form per unit volume of first fluid based on the droplet rate and droplet size;
the droplet size based on the magnitude of a pulse contained within the signal in response to the signal not crossing the second threshold signal level;
the droplet size based on the width of a pulse contained within the signal in response to the signal crossing the second threshold signal level; and
the droplet size based on the droplet rate.

6. The system according to claim 5, wherein the controller is further configured to detect a droplet of the second liquid of a predetermined size having an equivalent volume to a droplet of the second liquid having a spherical diameter in a range from 10 up to 1000 micrometers.

7. The system according claim 1, wherein the microfluidic channel comprises a converging-diverging nozzle.

8. The system according to claim 7, wherein:
the converging-diverging nozzle of the microfluidic channel comprises a contracting inlet portion and an expanding outlet portion along a flow direction; and
wherein a length of the contracting inlet portion is shorter than a length of the expanding outlet portion.

9. The system according to claim 1, wherein the microfluidic channel is at least one of:
at least partially submerged in the main flow of the vehicle engine fuel line, wherein an inlet of the microfluidic channel is positioned in the main flow of the vehicle engine fuel line or the inlet and an outlet of the microfluidic channel is positioned in the main flow of the vehicle engine fuel line; and
defined between two or more optical components selected from: the light source, the light detector, the light aperture, a light channel, a lens, and a separate microfluidic channel substrate.

10. The system according to claim 1, wherein the first fluid comprises a hydrocarbon fluid and the second fluid comprises water.

11. The system according to claim 1, further comprising at least one of:
a fuel line configured to deliver fuel to a fuel injector;
a fuel filter configured to filter water from gasoline or diesel fuel positioned along the fuel line; and
a fuel pump in fluid communication with the fuel line, wherein the fuel pump is configured to provide fuel flow to the fuel injector along the fuel line.

12. The system according to claim 1, further comprising another microfluidic channel positioned between the light source and the light detector.

13. The system according to claim 1, wherein the microfluidic channel defines a cross-sectional area less than 1 mm$^2$ and the light aperture has a width less than 1 mm to define the sensing area.

* * * * *

UNITED STATES PATENT AND TRADEMARK OFFICE
CERTIFICATE OF CORRECTION

PATENT NO. : 12,222,271 B2
APPLICATION NO. : 17/059189
DATED : February 11, 2025
INVENTOR(S) : Davis B. Moravec et al.

Page 1 of 1

It is certified that error appears in the above-identified patent and that said Letters Patent is hereby corrected as shown below:

In the Claims

In Claim 7, Line 38, 'according claim 1' should be --according to claim 1--.

Signed and Sealed this
Eighth Day of July, 2025

Coke Morgan Stewart
*Acting Director of the United States Patent and Trademark Office*